United States Patent [19]
Godowski et al.

[11] Patent Number: 6,030,831
[45] Date of Patent: Feb. 29, 2000

[54] TIE LIGAND HOMOLOGUES

[75] Inventors: Paul J. Godowski, Pacifica; Austin L. Gurney, Belmont, both of Calif.

[73] Assignee: Genetech, Inc., So. San Francisco, Calif.

[21] Appl. No.: 08/934,494

[22] Filed: Sep. 19, 1997

[51] Int. Cl.[7] ............ C12N 15/12; C12N 15/11; C12N 5/10; C07K 14/475
[52] U.S. Cl. ............ 435/320.1; 536/23.1; 536/23.5; 435/325; 435/252.3; 435/254.11; 435/69.1; 530/350
[58] Field of Search ............ 536/23.1, 23.5; 435/320.1, 325, 252.3, 254.11, 69.1; 530/350

[56] References Cited

U.S. PATENT DOCUMENTS

| | | | |
|---|---|---|---|
| 5,447,860 | 9/1995 | Ziegler | 435/240.1 |
| 5,521,073 | 5/1996 | Davis et al. | 435/69.5 |
| 5,643,755 | 7/1997 | Davis et al. | 435/69.5 |
| 5,650,490 | 7/1997 | Davis et al. | 530/350 |

FOREIGN PATENT DOCUMENTS

| | | |
|---|---|---|
| WO 93/14124 | 7/1993 | WIPO . |
| WO 95/13387 | 5/1995 | WIPO . |
| WO 95/21866 | 8/1995 | WIPO . |
| WO 95/26364 | 10/1995 | WIPO . |
| WO 96/09381 | 3/1996 | WIPO . |
| WO 96/11269 | 4/1996 | WIPO . |
| WO 96/31598 | 10/1996 | WIPO . |
| WO 97/48804 | 12/1997 | WIPO . |

OTHER PUBLICATIONS

Hanahan, D., Signaling vascular morphogenesis and maintenance, Science, 277: 48–50, Jul. 1997.
Davis et al. *Cell* 87:1161–1169 (1996).
Dumont et al. *Oncogene* 8:1293–1301 (1993).
Kaipainen et al. *Cander Res.* 54:6571–6577 (1994).
Korhonen et al. *Blood* 80:2548–2555 (1992).
Maisonpierre et al. *Oncogene* 8:1631–1637 (1993).
Partanen et al., "Putative Tyrosine Kinases Expressed in K–562 Human Leukemia Cells" *Proc. Natl. Acad. Sci.* 87:8913–8917 (1990).
Suri et al. *Cell* 87:1171–1180 (1996).
Maisonpierre et al., "Angiopoietin–2, a Natural Antagonist for Tie2 that Disrupts in vivo Disrupts in vivo Angiogenesis" *Science*277:55–60 (Jul. 4, 1997).

*Primary Examiner*—Lorraine Spector
*Assistant Examiner*—Claire M. Kaufman
*Attorney, Agent, or Firm*—Mark T. Kresnak

[57] ABSTRACT

The present invention concerns isolated nucleic acid molecules encoding the novel TIE ligands NL2, NL3 and FLS139, the proteins encoded by such nucleic acid molecules, as well as methods and means for making and using such nucleic acid and protein molecules.

15 Claims, 13 Drawing Sheets

SEQ ID NO:1:

```
GCCGAGCTGA GCGGATCCTC ACATGACTGT GATCCGATTC TTTCCAGCGG 50
CTTCTGCAAC CAAGCGGGTC TTACCCCCGG TCCTCCGCGT CTCCAGTCCT 100
CGCACCTGGA ACCCCAACGT CCCCGAGAGT CCCCGAATCC CCGCTCCAG 150
GCTACCTAAG AGGATGAGCG GTGCTCCGAC GGCCGGGGCA GCCCTGATGC 200
TCTGCCGC CACCGCCGTG CTACTGAGCG CTCAGGGCGG ACCCGTGCAG 250
TCCAAGTCGC CGCGCTTTGC GTCCTGGGAC GAGATGAATG TCCTGGCGCA 300
CGGACTCCTG CAGCTCGGCC AGGGGCTGCG CGAACACGCG GAGCGCACCC 350
GCAGTCAGCT GAGCGCGCTG GAGCGGCGCC TGAGCGCGTG CGGGTCCGCC 400
TGTCAGGGAA CCGAGGGGTC CACCGACCTC CCGTTAGCCC CTGAGAGCCG 450
GGTGGACCCT GAGGTCCTTC ACAGCCTGCA GACACAACTC AAGGCTCAGA 500
ACAGCAGGAT CCAGCAACTC TTCCACAAGG TGGCCCAGCA GCAGCGGCAC 550
CTGGAGAAGC AGCACCTGCG AATTCAGCAT CTGCAAAGCC AGTTTGGCCT 600
CCTGGACCAC AAGCACCTAG ACCATGAGGT GGCCAAGCCT GCCCGAAGAA 650
AGAGGCTGCC CGAGATGGCC CAGCCAGTTG ACCCGGCTCA CAATGTCAGC 700
CGCCTGCACC GGCTGCCCAG GGATTGCCAG GAGCTGTTCC AGGTTGGGGA 750
GAGGCAGAGT GGACTATTTG AAATCCAGCC TCAGGGGTCT CCGCCATTTT 800
TGGTGAACTG CAAGATGACC TCAGATGGAG GCTGGACAGT AATTCAGAGG 850
CGCCACGATG GCTCAGTGGA CTTCAACCGG CCCTGGGAAG CCTACAAGGC 900
GGGGTTTGGG GATCCCCACG GCGAGTTCTG GCTGGGTCTG GAGAAGGTGC 950
ATAGCATCAC GGGGGACCGC AACAGCCGCC TGGCCGTGCA GCTGCGGGAC 1000
TGGGATGGCA ACGCCGAGTT GCTGCAGTTC TCCGTGCACC TGGGTGGCGA 1050
GGACACGGCC TATAGCCTGC AGCTCACTGC ACCCGTGGCC GGCCAGCTGG 1100
GCGCCACCAC CGTCCCACCC AGCGGCCTCT CCGTACCCTT CTCCACTTGG 1150
```

FIG. 2A

```
GACCAGGATC ACGACCTCCG CAGGGACAAG AACTGCGCCA AGAGCCTCTC 1200

TGGAGGCTGG TGGTTTGGCA CCTGCAGCCA TTCCAACCTC AACGGCCAGT 1250

ACTTCCGCTC CATCCCACAG CAGCGGCAGA AGCTTAAGAA GGGAATCTTC 1300

TGGAAGACCT GGCGGGGCCG CTACTACCCG CTGCAGGCCA CCACCATGTT 1350

GATCCAGCCC ATGGCAGCAG AGGCAGCCTC CTAGCGTCCT GGCTGGGCCT 1400

GGTCCCAGGC CCACGAAAGA CGGTGACTCT TGGCTCTGCC CGAGGATGTG 1450

GCCGTTCCCT GCCTGGGCAG GGGCTCCAAG GAGGGGCCAT CTGGAAACTT 1500

GTGGACAGAG AAGAAGACCA CGACTGGAGA AGCCCCCTTT CTGAGTGCAG 1550

GGGGGCTGCA TGCGTTGCCT CCTGAGATCG AGGCTGCAGG ATATGCTCAG 1600

ACTCTAGAGG CGTGGACCAA GGGGCATGGA GCTTCACTCC TTGCTGGCCA 1650

GGGAGTTGGG GACTCAGAGG GACCACTTGG GGCCAGCCAG ACTGGCCTCA 1700

ATGGCGGACT CAGTCACATT GACTGACGGG GACCAGGGCT TGTGTGGGTC 1750

GAGAGCGCCC TCATGGTGCT GGTGCTGTTG TGTGTAGGTC CCCTGGGGAC 1800

ACAAGCAGGC GCCAATGGTA TCTGGGCGGA GCTCACAGAG TTCTTGGAAT 1850

AAAAGCAACC TCAGAACAC 1869
```

FIG. 2B

SEQ ID NO:2:

```
Met Ser Gly Ala Pro Thr Ala Gly Ala Ala Leu Met Leu Cys Ala
 1               5                  10                  15

Ala Thr Ala Val Leu Leu Ser Ala Gln Gly Gly Pro Val Gln Ser
                20                  25                  30

Lys Ser Pro Arg Phe Ala Ser Trp Asp Glu Met Asn Val Leu Ala
                35                  40                  45

His Gly Leu Leu Gln Leu Gly Gln Gly Leu Arg Glu His Ala Glu
                50                  55                  60

Arg Thr Arg Ser Gln Leu Ser Ala Leu Glu Arg Arg Leu Ser Ala
                65                  70                  75

Cys Gly Ser Ala Cys Gln Gly Thr Glu Gly Ser Thr Asp Leu Pro
                80                  85                  90

Leu Ala Pro Glu Ser Arg Val Asp Pro Glu Val Leu His Ser Leu
                95                  100                 105

Gln Thr Gln Leu Lys Ala Gln Asn Ser Arg Ile Gln Gln Leu Phe
                110                 115                 120

His Lys Val Ala Gln Gln Gln Arg His Leu Glu Lys Gln His Leu
                125                 130                 135

Arg Ile Gln His Leu Gln Ser Gln Phe Gly Leu Leu Asp His Lys
                140                 145                 150

His Leu Asp His Glu Val Ala Lys Pro Ala Arg Arg Lys Arg Leu
                155                 160                 165

Pro Glu Met Ala Gln Pro Val Asp Pro Ala His Asn Val Ser Arg
                170                 175                 180

Leu His Arg Leu Pro Arg Asp Cys Gln Glu Leu Phe Gln Val Gly
                185                 190                 195

Glu Arg Gln Ser Gly Leu Phe Glu Ile Gln Pro Gln Gly Ser Pro
                200                 205                 210

Pro Phe Leu Val Asn Cys Lys Met Thr Ser Xaa Gly Gly Trp Thr
                215                 220                 225

Val Ile Gln Arg Arg His Asp Gly Ser Val Asp Phe Asn Arg Pro
                230                 235                 240
```

FIG. 3A

| | | | | | | | | | | | |
|---|---|---|---|---|---|---|---|---|---|---|---|
| Trp | Glu | Ala | Tyr | Lys | Ala | Gly | Phe | Gly | Asp | Pro | His | Gly | Glu | Phe |

Trp Glu Ala Tyr Lys Ala Gly Phe Gly Asp Pro His Gly Glu Phe
            245                250                255

Trp Leu Gly Leu Glu Lys Val His Ser Ile Thr Gly Asp Arg Asn
            260                265                270

Ser Arg Leu Ala Val Gln Leu Arg Asp Trp Asp Gly Asn Ala Glu
            275                280                285

Leu Leu Gln Phe Ser Val His Leu Gly Gly Glu Asp Thr Ala Tyr
            290                295                300

Ser Leu Gln Leu Thr Ala Pro Val Ala Gly Gln Leu Gly Ala Thr
            305                310                315

Thr Val Pro Pro Ser Gly Leu Ser Val Pro Phe Ser Thr Trp Asp
            320                325                330

Gln Asp His Asn Leu Arg Arg Asp Lys Asn Cys Ala Lys Ser Leu
            335                340                345

Ser Gly Gly Trp Trp Phe Gly Thr Cys Ser His Ser Asn Leu Asn
            350                355                360

Gly Gln Tyr Phe Arg Ser Ile Pro Gln Gln Arg Gln Lys Leu Lys
            365                370                375

Lys Gly Ile Phe Trp Lys Thr Trp Arg Gly Arg Tyr Tyr Pro Leu
            380                385                390

Gln Ala Thr Thr Met Leu Ile Gln Pro Met Ala Ala Glu Ala Ala
            395                400                405

Ser
406

FIG. 3B

SEQ ID NO:3:

| CGGACGCGTG | GGCCCCTGGT | GGGCCCAGCA | AGATGGATCT | ACTGTGGATC | 50 |
| CTGCCCTCCC | TGTGGCTTCT | CCTGCTTGGG | GGGCCTGCCT | GCCTGAAGAC | 100 |
| CCAGGAACAC | CCCAGCTGCC | CAGGACCCAG | GGAACTGGAA | GCCAGCAAAG | 150 |
| TTGTCCTCCT | GCCCAGTTGT | CCCGGAGCTC | CAGGAAGTCC | TGGGGAGAAG | 200 |
| GGAGCCCCAG | GTCCTCAAGG | GCCACCTGGA | CCACCAGGCA | AGATGGGCCC | 250 |
| CAAGGGTGAG | CCAGGCCCCA | GAAACTGCCG | GGAGCTGTTG | AGCCAGGGCG | 300 |
| CCACCTTGAG | CGGCTGGTAC | CATCTGTGCC | TACCTGAGGG | CAGGGCCCTC | 350 |
| CCAGTCTTTT | GTGACATGGA | CACCGAGGGG | GGCGGCTGGC | TGGTGTTTCA | 400 |
| GAGGCGCCAG | GATGGTTCTG | TGGATTTCTT | CCGCTCTTGG | TCCTCCTACA | 450 |
| GAGCAGGTTT | TGGGAACCAA | GAGTCTGAAT | TCTGGCTGGG | AAATGAGAAT | 500 |
| TTGCACCAGC | TTACTCTCCA | GGGTAACTGG | GAGCTGCGGG | TAGAGCTGGA | 550 |
| AGACTTTAAT | GGTAACCGTA | CTTTCGCCCA | CTATGCGACC | TTCCGCCTCC | 600 |
| TCGGTGAGGT | AGACCACTAC | CAGCTGGCAC | TGGGCAAGTT | CTCAGAGGGC | 650 |
| ACTGCAGGGG | ATTCCCTGAG | CCTCCACAGT | GGGAGGCCCT | TTACCACCTA | 700 |
| TGACGCTGAC | CACGATTCAA | GCAACAGCAA | CTGTGCAGTG | ATTGTCCACG | 750 |
| GTGCCTGGTG | GTATGCATCC | TGTTACCGAT | CAAATCTCAA | TGGTCGCTAT | 800 |
| GCAGTGTCTG | AGGCTGCCGC | CCACAAATAT | GGCATTGACT | GGGCCTCAGG | 850 |
| CCGTGGTGTG | GGCCACCCCT | ACCGCAGGGT | TCGGATGATG | CTTCGATAGG | 900 |
| GCACTCTGGC | AGCCAGTGCC | CTTATCTCTC | CTGTACAGCT | TCCGGATCGT | 950 |
| CAGCCACCTT | GCCTTTGCCA | ACCACCTCTG | CTTGCCTGTC | CACATTTAAA | 1000 |
| AATAAAATCA | TTTTAGCCCT | TTCA | | | 1024 |

FIG. 4

SEQ ID NO:4:

```
Met Asp Leu Leu Trp Ile Leu Pro Ser Leu Trp Leu Leu Leu Leu
 1               5                  10                  15

Gly Gly Pro Ala Cys Leu Lys Thr Gln Glu His Pro Ser Cys Pro
                20                  25                  30

Gly Pro Arg Glu Leu Glu Ala Ser Lys Val Val Leu Leu Pro Ser
                35                  40                  45

Cys Pro Gly Ala Pro Gly Ser Pro Gly Glu Lys Gly Ala Pro Gly
                50                  55                  60

Pro Gln Gly Pro Pro Gly Pro Pro Gly Lys Met Gly Pro Lys Gly
                65                  70                  75

Glu Pro Gly Pro Arg Asn Cys Arg Glu Leu Leu Ser Gln Gly Ala
                80                  85                  90

Thr Leu Ser Gly Trp Tyr His Leu Cys Leu Pro Glu Gly Arg Ala
                95                  100                 105

Leu Pro Val Phe Cys Asp Met Asp Thr Glu Gly Gly Gly Trp Leu
                110                 115                 120

Val Phe Gln Arg Arg Gln Asp Gly Ser Val Asp Phe Phe Arg Ser
                125                 130                 135

Trp Ser Ser Tyr Arg Ala Gly Phe Gly Asn Gln Glu Ser Glu Phe
                140                 145                 150

Trp Leu Gly Asn Glu Asn Leu His Gln Leu Thr Leu Gln Gly Asn
                155                 160                 165

Trp Glu Leu Arg Val Glu Leu Glu Asp Phe Asn Gly Asn Arg Thr
                170                 175                 180

Phe Ala His Tyr Ala Thr Phe Arg Leu Leu Gly Glu Val Asp His
                185                 190                 195

Tyr Gln Leu Ala Leu Gly Lys Phe Ser Glu Gly Thr Ala Gly Asp
                200                 205                 210

Ser Leu Ser Leu His Ser Gly Arg Pro Phe Thr Thr Tyr Asp Ala
                215                 220                 225

Asp His Asp Ser Ser Asn Ser Asn Cys Ala Val Ile Val His Gly
                230                 235                 240

Ala Trp Trp Tyr Ala Ser Cys Tyr Arg Ser Asn Leu Asn Gly Arg
                245                 250                 255

Tyr Ala Val Ser Glu Ala Ala Ala His Lys Tyr Gly Ile Asp Trp
                260                 265                 270

Ala Ser Gly Arg Gly Val Gly His Pro Tyr Arg Arg Val Arg Met
                275                 280                 285

Met Leu Arg
     288
```

FIG. 5

SEQ ID NO:5:

```
GCGGACGCGT GGGTGAAATT GAAAATCAAG ATAAAAATGT TCACAATTAA 50
GCTCCTTCTT TTTATTGTTC CTCTAGTTAT TTCCTCCAGA ATTGATCAAG 100
ACAATTCATC ATTTGATTCT CTATCTCCAG AGCCAAAATC AAGATTTGCT 150
ATGTTAGACG ATGTAAAAAT TTTAGCCAAT GGCCTCCTTC AGTTGGGACA 200
TGGTCTTAAA GACTTTGTCC ATAAGACGAA GGGCCAAATT AATGACATAT 250
TTCAAAAACT CAACATATTT GATCAGTCTT TTTATGATCT ATCGCTGCAA 300
ACCAGTGAAA TCAAAGAAGA AGAAAAGGAA CTGAGAAGAA CTACATATAA 350
ACTACAAGTC AAAAATGAAG AGGTAAAGAA TATGTCACTT GAACTCAACT 400
CAAAACTTGA AAGCCTCCTA GAAGAAAAAA TTCTACTTCA ACAAAAAGTG 450
AAATATTTAG AAGAGCAACT AACTAACTTA ATTCAAAATC AACCTGAAAC 500
TCCAGAACAC CCAGAAGTAA CTTCACTTAA AACTTTTGTA GAAAAACAAG 550
ATAATAGCAT CAAAGACCTT CTCCAGACCG TGGAAGACCA ATATAAACAA 600
TTAAACCAAC AGCATAGTCA AATAAAAGAA ATAGAAAATC AGCTCAGAAG 650
GACTAGTATT CAAGAACCCA CAGAAATTTC TCTATCTTCC AAGCCAAGAG 700
CACCAAGAAC TACTCCCTTT CTTCAGTTGA ATGAAATAAG AAATGTAAAA 750
CATGATGGCA TTCCTGCTGA ATGTACCACC ATTTATAACA GAGGTGAACA 800
TACAAGTGGC ATGTATGCCA TCAGACCCAG CAACTCTCAA GTTTTTCATG 850
TCTACTGTGA TGTTATATCA GGTAGTCCAT GGACATTAAT TCAACATCGA 900
ATAGATGGAT CACAAAACTT CAATGAAACG TGGGAGAACT ACAAATATGG 950
TTTTGGGAGG CTTGATGGAG AATTTTGGTT GGGCCTAGAG AAGATATACT 1000
CCATAGTGAA GCAATCTAAT TATGTTTTAC GAATTGAGTT GGAAGACTGG 1050
AAAGACAACA AACATTATAT TGAATATTCT TTTTACTTGG GAAATCACGA 1100
AACCAACTAT ACGCTACATC TAGTTGCGAT TACTGGCAAT GTCCCCAATG 1150
```

FIG. 6A

```
CAATCCCGGA AAACAAAGAT TTGGTGTTTT CTACTTGGGA TCACAAAGCA 1200

AAAGGACACT TCAACTGTCC AGAGGGTTAT TCAGGAGGCT GGTGGTGGCA 1250

TGATGAGTGT GGAGAAAACA ACCTAAATGG TAAATATAAC AAACCAAGAG 1300

CAAAATCTAA GCCAGAGAGG AGAAGAGGAT TATCTTGGAA GTCTCAAAAT 1350

GGAAGGTTAT ACTCTATAAA ATCAACCAAA ATGTTGATCC ATCCAACAGA 1400

TTCAGAAAGC TTTGAATGAA CTGAGGCAAT TTAAAGGCAT ATTTAACCAT 1450

TAACTCATTC CAAGTTAATG TGGTCTAATA ATCTGGTATA AATCCTTAAG 1500

AGAAAGCTTG AGAAATAGAT TTTTTTTATC TTAAAGTCAC TGTCTATTTA 1550

AGATTAAACA TACAATCACA TAACCTTAAA GAATACCGTT TACATTTCTC 1600

AATCAAAATT CTTATAATAC TATTTGTTTT AAATTTGTG ATGTGGGAAT 1650

CAATTTTAGA TGGTCACAAT CTAGATTATA ATCAATAGGT GAACTTATTA 1700

AATAACTTTT CTAAATAAAA AATTTAGAGA CTTTTATTTT AAAAGGCATC 1750

ATATGAGCTA ATATCACAAC TTTCCCAGTT TAAAAAACTA GTACTCTTGT 1800

TAAAACTCTA AACTTGACTA AATACAGAGG ACTGGTAATT GTACAGTTCT 1850

TAAATGTTGT AGTATTAATT TCAAAACTAA AAATCGTCAG CACAGAGTAT 1900

GTGTAAAAAT CTGTAATACA AATTTTTAAA CTGATGCTTC ATTTTGCTAC 1950

AAAATAATTT GGAGTAAATG TTTGATATGA TTTATTTATG AAACCTAATG 2000

AAGCAGAATT AAATACTGTA TTAAAATAAG TTCGCTGTCT TT 2042
```

FIG. 6B

SEQ ID NO:6:

| | | | | | | | | | | | | | | |
|---|---|---|---|---|---|---|---|---|---|---|---|---|---|---|
|Met|Phe|Thr|Ile|Lys|Leu|Leu|Phe|Ile|Val|Pro|Leu|Val|Ile|
|1| | | |5| | | |10| | | | |15|

Ser Ser Arg Ile Asp Gln Asp Asn Ser Ser Phe Asp Ser Leu Ser
                20                  25                  30

Pro Glu Pro Lys Ser Arg Phe Ala Met Leu Asp Asp Val Lys Ile
                35                  40                  45

Leu Ala Asn Gly Leu Leu Gln Leu Gly His Gly Leu Lys Asp Phe
                50                  55                  60

Val His Lys Thr Lys Gly Gln Ile Asn Asp Ile Phe Gln Lys Leu
                65                  70                  75

Asn Ile Phe Asp Gln Ser Phe Tyr Asp Leu Ser Leu Gln Thr Ser
                80                  85                  90

Glu Ile Lys Glu Glu Glu Lys Glu Leu Arg Arg Thr Thr Tyr Lys
                95                  100                 105

Leu Gln Val Lys Asn Glu Glu Val Lys Asn Met Ser Leu Glu Leu
                110                 115                 120

Asn Ser Lys Leu Glu Ser Leu Leu Glu Glu Lys Ile Leu Leu Gln
                125                 130                 135

Gln Lys Val Lys Tyr Leu Glu Glu Gln Leu Thr Asn Leu Ile Gln
                140                 145                 150

Asn Gln Pro Glu Thr Pro Glu His Pro Glu Val Thr Ser Leu Lys
                155                 160                 165

Thr Phe Val Glu Lys Gln Asp Asn Ser Ile Lys Asp Leu Leu Gln
                170                 175                 180

Thr Val Glu Asp Gln Tyr Lys Gln Leu Asn Gln Gln His Ser Gln
                185                 190                 195

Ile Lys Glu Ile Glu Asn Gln Leu Arg Arg Thr Ser Ile Gln Glu
                200                 205                 210

Pro Thr Glu Ile Ser Leu Ser Ser Lys Pro Arg Ala Pro Arg Thr
                215                 220                 225

Thr Pro Phe Leu Gln Leu Asn Glu Ile Arg Asn Val Lys His Asp
                230                 235                 240

FIG. 7A

```
Gly Ile Pro Ala Glu Cys Thr Thr Ile Tyr Asn Arg Gly Glu His
            245             250             255

Thr Ser Gly Met Tyr Ala Ile Arg Pro Ser Asn Ser Gln Val Phe
            260             265             270

His Val Tyr Cys Asp Val Ile Ser Gly Ser Pro Trp Thr Leu Ile
            275             280             285

Gln His Arg Ile Asp Gly Ser Gln Asn Phe Asn Glu Thr Trp Glu
            290             295             300

Asn Tyr Lys Tyr Gly Phe Gly Arg Leu Asp Gly Glu Phe Trp Leu
            305             310             315

Gly Leu Glu Lys Ile Tyr Ser Ile Val Lys Gln Ser Asn Tyr Val
            320             325             330

Leu Arg Ile Glu Leu Glu Asp Trp Lys Asp Asn Lys His Tyr Ile
            335             340             345

Glu Tyr Ser Phe Tyr Leu Gly Asn His Glu Thr Asn Tyr Thr Leu
            350             355             360

His Leu Val Ala Ile Thr Gly Asn Val Pro Asn Ala Ile Pro Glu
            365             370             375

Asn Lys Asp Leu Val Phe Ser Thr Trp Asp His Lys Ala Lys Gly
            380             385             390

His Phe Asn Cys Pro Glu Gly Tyr Ser Gly Gly Trp Trp Trp His
            395             400             405

Asp Glu Cys Gly Glu Asn Asn Leu Asn Gly Lys Tyr Asn Lys Pro
            410             415             420

Arg Ala Lys Ser Lys Pro Glu Arg Arg Gly Leu Ser Trp Lys
            425             430             435

Ser Gln Asn Gly Arg Leu Tyr Ser Ile Lys Ser Thr Lys Met Leu
            440             445             450

Ile His Pro Thr Asp Ser Glu Ser Phe Glu
            455             460
```

FIG. 7B

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 1869 base pairs
        (B) TYPE: Nucleic Acid
        (C) STRANDEDNESS: Single
        (D) TOPOLOGY: Linear (xi) SEQUENCE DESCRIPTION: SEQ ID NO:1:

```
GCCGAGCTGA GCGGATCCTC ACATGACTGT GATCCGATTC TTTCCAGCGG           50
CTTCTGCAAC CAAGCGGGTC TTACCCCCGG TCCTCCGCGT CTCCAGTCCT          100
CGCACCTGGA ACCCCAACGT CCCCGAGAGT CCCCGAATCC CCGCTCCCAG          150
GCTACCTAAG AGGATGAGCG GTGCTCCGAC GGCCGGGGCA GCCCTGATGC          200
TCTGCGCCGC CACCGCCGTG CTACTGAGCG CTCAGGGCGG ACCCGTGCAG          250
TCCAAGTCGC CGCGCTTTGC GTCCTGGGAC GAGATGAATG TCCTGGCGCA          300
CGGACTCCTG CAGCTCGGCC AGGGGCTGCG CGAACACGCG GAGCGCACCC          350
GCAGTCAGCT GAGCGCGCTG GAGCGGCGCC TGAGCGCGTG CGGGTCCGCC          400
TGTCAGGGAA CCGAGGGGTC CACCGACCTC CCGTTAGCCC CTGAGAGCCG          450
GGTGGACCCT GAGGTCCTTC ACAGCCTGCA GACACAACTC AAGGCTCAGA          500
ACAGCAGGAT CCAGCAACTC TTCCACAAGG TGGCCCAGCA GCAGCGGCAC          550
CTGGAGAAGC AGCACCTGCG AATTCAGCAT CTGCAAAGCC AGTTTGGCCT          600
CCTGGACCAC AAGCACCTAG ACCATGAGGT GGCCAAGCCT GCCCGAAGAA          650
AGAGGCTGCC CGAGATGGCC CAGCCAGTTG ACCCGGCTCA CAATGTCAGC          700
CGCCTGCACC GGCTGCCCAG GGATTGCCAG GAGCTGTTCC AGGTTGGGGA          750
GAGGCAGAGT GGACTATTTG AAATCCAGCC TCAGGGGTCT CCGCCATTTT          800
TGGTGAACTG CAAGATGACC TCAGATGGAG GCTGGACAGT AATTCAGAGG          850
CGCCACGATG GCTCAGTGGA CTTCAACCGG CCCTGGGAAG CCTACAAGGC          900
GGGGTTTGGG GATCCCCACG GCGAGTTCTG GCTGGGTCTG GAGAAGGTGC          950
ATAGCATCAC GGGGGACCGC AACAGCCGCC TGGCCGTGCA GCTGCGGGAC         1000
TGGGATGGCA ACGCCGAGTT GCTGCAGTTC TCCGTGCACC TGGGTGGCGA         1050
GGACACGGCC TATAGCCTGC AGCTCACTGC ACCCGTGGCC GGCCAGCTGG         1100
GCGCCACCAC CGTCCCACCC AGCGGCCTCT CCGTACCCTT CTCCACTTGG         1150
GACCAGGATC ACGACCTCCG CAGGGACAAG AACTGCGCCA GAGCCTCTC          1200
TGGAGGCTGG TGGTTTGGCA CCTGCAGCCA TTCCAACCTC AACGGCCAGT         1250
ACTTCCGCTC CATCCCACAG CAGCGGCAGA AGCTTAAGAA GGGAATCTTC         1300
TGGAAGACCT GGCGGGGCCG CTACTACCCG CTGCAGGCCA CCACCATGTT         1350
GATCCAGCCC ATGGCAGCAG AGGCAGCCTC CTAGCGTCCT GGCTGGGCCT         1400
GGTCCCAGGC CCACGAAAGA CGGTGACTCT TGGCTCTGCC CGAGGATGTG         1450
GCCGTTCCCT GCCTGGGCAG GGGCTCCAAG GAGGGGCCAT CTGGAAACTT         1500
GTGGACAGAG AAGAAGACCA CGACTGGAGA AGCCCCCTTT CTGAGTGCAG         1550
GGGGGCTGCA TGCGTTGCCT CCTGAGATCG AGGCTGCAGG ATATGCTCAG         1600
ACTCTAGAGG CGTGGACCAA GGGGCATGGA GCTTCACTCC TTGCTGGCCA         1650
GGGAGTTGGG GACTCAGAGG GACCACTTGG GGCCAGCCAG ACTGGCCTCA         1700
```

```
ATGGCGGACT CAGTCACATT GACTGACGGG GACCAGGGCT TGTGTGGGTC            1750

GAGAGCGCCC TCATGGTGCT GGTGCTGTTG TGTGTAGGTC CCCTGGGGAC            1800

ACAAGCAGGC GCCAATGGTA TCTGGGCGGA GCTCACAGAG TTCTTGGAAT            1850

AAAAGCAACC TCAGAACAC                                             1869
```

(2) INFORMATION FOR SEQ ID NO:2:

(i) SEQUENCE CHARACTERISTICS:
        (A) LENGTH: 406 amino acids
        (B) TYPE: Amino Acid
        (D) TOPOLOGY: Linear (xi) SEQUENCE DESCRIPTION: SEQ ID NO:2:

```
Met Ser Gly Ala Pro Thr Ala Gly Ala Ala Leu Met Leu Cys Ala
 1               5                  10                  15

Ala Thr Ala Val Leu Leu Ser Ala Gln Gly Gly Pro Val Gln Ser
                20                  25                  30

Lys Ser Pro Arg Phe Ala Ser Trp Asp Glu Met Asn Val Leu Ala
                35                  40                  45

His Gly Leu Leu Gln Leu Gly Gln Gly Leu Arg Glu His Ala Glu
                50                  55                  60

Arg Thr Arg Ser Gln Leu Ser Ala Leu Glu Arg Arg Leu Ser Ala
                65                  70                  75

Cys Gly Ser Ala Cys Gln Gly Thr Glu Gly Ser Thr Asp Leu Pro
                80                  85                  90

Leu Ala Pro Glu Ser Arg Val Asp Pro Glu Val Leu His Ser Leu
                95                 100                 105

Gln Thr Gln Leu Lys Ala Gln Asn Ser Arg Ile Gln Gln Leu Phe
               110                 115                 120

His Lys Val Ala Gln Gln Arg His Leu Glu Lys Gln His Leu
               125                 130                 135

Arg Ile Gln His Leu Gln Ser Gln Phe Gly Leu Leu Asp His Lys
               140                 145                 150

His Leu Asp His Glu Val Ala Lys Pro Ala Arg Arg Lys Arg Leu
               155                 160                 165

Pro Glu Met Ala Gln Pro Val Asp Pro Ala His Asn Val Ser Arg
               170                 175                 180

Leu His Arg Leu Pro Arg Asp Cys Gln Glu Leu Phe Gln Val Gly
               185                 190                 195

Glu Arg Gln Ser Gly Leu Phe Glu Ile Gln Pro Gln Gly Ser Pro
               200                 205                 210

Pro Phe Leu Val Asn Cys Lys Met Thr Ser Xaa Gly Gly Trp Thr
               215                 220                 225

Val Ile Gln Arg Arg His Asp Gly Ser Val Asp Phe Asn Arg Pro
               230                 235                 240

Trp Glu Ala Tyr Lys Ala Gly Phe Gly Asp Pro His Gly Glu Phe
               245                 250                 255

Trp Leu Gly Leu Glu Lys Val His Ser Ile Thr Gly Asp Arg Asn
               260                 265                 270

Ser Arg Leu Ala Val Gln Leu Arg Asp Trp Asp Gly Asn Ala Glu
               275                 280                 285

Leu Leu Gln Phe Ser Val His Leu Gly Gly Glu Asp Thr Ala Tyr
               290                 295                 300
```

```
Ser Leu Gln Leu Thr Ala Pro Val Ala Gly Gln Leu Gly Ala Thr
            305                 310                 315

Thr Val Pro Pro Ser Gly Leu Ser Val Pro Phe Ser Thr Trp Asp
            320                 325                 330

Gln Asp His Asn Leu Arg Arg Asp Lys Asn Cys Ala Lys Ser Leu
            335                 340                 345

Ser Gly Gly Trp Trp Phe Gly Thr Cys Ser His Ser Asn Leu Asn
            350                 355                 360

Gly Gln Tyr Phe Arg Ser Ile Pro Gln Gln Arg Gln Lys Leu Lys
            365                 370                 375

Lys Gly Ile Phe Trp Lys Thr Trp Arg Gly Arg Tyr Tyr Pro Leu
            380                 385                 390

Gln Ala Thr Thr Met Leu Ile Gln Pro Met Ala Ala Glu Ala Ala
            395                 400                 405

Ser
406

(2) INFORMATION FOR SEQ ID NO:3:

(i) SEQUENCE CHARACTERISTICS:
        (A) LENGTH: 1024 base pairs
        (B) TYPE: Nucleic Acid
        (C) STRANDEDNESS: Single
        (D) TOPOLOGY: Linear (xi) SEQUENCE DESCRIPTION: SEQ ID NO:3:

CGGACGCGTG GGCCCCTGGT GGGCCCAGCA AGATGGATCT ACTGTGGATC            50

CTGCCCTCCC TGTGGCTTCT CCTGCTTGGG GGGCCTGCCT GCCTGAAGAC           100

CCAGGAACAC CCCAGCTGCC CAGGACCCAG GGAACTGGAA GCCAGCAAAG           150

TTGTCCTCCT GCCCAGTTGT CCCGGAGCTC AGGAAGTCC  TGGGGAGAAG           200

GGAGCCCCAG GTCCTCAAGG GCCACCTGGA CCACCAGGCA AGATGGGCCC           250

CAAGGGTGAG CCAGGCCCCA GAAACTGCCG GGAGCTGTTG AGCCAGGGCG           300

CCACCTTGAG CGGCTGGTAC CATCTGTGCC TACCTGAGGG CAGGGCCCTC           350

CCAGTCTTTT GTGACATGGA CACCGAGGGG GGCGGCTGGC TGGTGTTTCA           400

GAGGCGCCAG GATGGTTCTG TGGATTTCTT CCGCTCTTGG TCCTCCTACA           450

GAGCAGGTTT TGGGAACCAA GAGTCTGAAT TCTGGCTGGG AAATGAGAAT           500

TTGCACCAGC TTACTCTCCA GGGTAACTGG GAGCTGCGGG TAGAGCTGGA           550

AGACTTTAAT GGTAACCGTA CTTTCGCCCA CTATGCGACC TTCCGCCTCC           600

TCGGTGAGGT AGACCACTAC CAGCTGGCAC TGGGCAAGTT CTCAGAGGGC           650

ACTGCAGGGG ATTCCCTGAG CCTCCACAGT GGGAGGCCCT TTACCACCTA           700

TGACGCTGAC CACGATTCAA GCAACAGCAA CTGTGCAGTG ATTGTCCACG           750

GTGCCTGGTG GTATGCATCC TGTTACCGAT CAAATCTCAA TGGTCGCTAT           800

GCAGTGTCTG AGGCTGCCGC CCACAAATAT GGCATTGACT GGGCCTCAGG           850

CCGTGGTGTG GGCCACCCCT ACCGCAGGGT TCGGATGATG CTTCGATAGG           900

GCACTCTGGC AGCCAGTGCC CTTATCTCTC CTGTACAGCT TCCGGATCGT           950

CAGCCACCTT GCCTTTGCCA ACCACCTCTG CTTGCCTGTC CACATTTAAA          1000

AATAAAATCA TTTTAGCCCT TTCA                                      1024

(2) INFORMATION FOR SEQ ID NO:4:
```

(i) SEQUENCE CHARACTERISTICS:
    (A) LENGTH: 288 amino acids
    (B) TYPE: Amino Acid
    (D) TOPOLOGY: Linear (xi) SEQUENCE DESCRIPTION: SEQ ID NO:4:

```
Met Asp Leu Leu Trp Ile Leu Pro Ser Leu Trp Leu Leu Leu
 1               5                  10                  15

Gly Gly Pro Ala Cys Leu Lys Thr Gln Glu His Pro Ser Cys Pro
                20                  25                  30

Gly Pro Arg Glu Leu Glu Ala Ser Lys Val Leu Leu Pro Ser
                35                  40                  45

Cys Pro Gly Ala Pro Gly Ser Pro Gly Glu Lys Gly Ala Pro Gly
                50                  55                  60

Pro Gln Gly Pro Pro Gly Pro Pro Gly Lys Met Gly Pro Lys Gly
                65                  70                  75

Glu Pro Gly Pro Arg Asn Cys Arg Glu Leu Leu Ser Gln Gly Ala
                80                  85                  90

Thr Leu Ser Gly Trp Tyr His Leu Cys Leu Pro Glu Gly Arg Ala
                95                  100                 105

Leu Pro Val Phe Cys Asp Met Asp Thr Glu Gly Gly Gly Trp Leu
                110                 115                 120

Val Phe Gln Arg Arg Gln Asp Gly Ser Val Asp Phe Arg Ser
                125                 130                 135

Trp Ser Ser Tyr Arg Ala Gly Phe Gly Asn Gln Glu Ser Glu Phe
                140                 145                 150

Trp Leu Gly Asn Glu Asn Leu His Gln Leu Thr Leu Gln Gly Asn
                155                 160                 165

Trp Glu Leu Arg Val Glu Leu Glu Asp Phe Asn Gly Asn Arg Thr
                170                 175                 180

Phe Ala His Tyr Ala Thr Phe Arg Leu Leu Gly Glu Val Asp His
                185                 190                 195

Tyr Gln Leu Ala Leu Gly Lys Phe Ser Glu Gly Thr Ala Gly Asp
                200                 205                 210

Ser Leu Ser Leu His Ser Gly Arg Pro Phe Thr Thr Tyr Asp Ala
                215                 220                 225

Asp His Asp Ser Ser Asn Ser Asn Cys Ala Val Ile Val His Gly
                230                 235                 240

Ala Trp Trp Tyr Ala Ser Cys Tyr Arg Ser Asn Leu Asn Gly Arg
                245                 250                 255

Tyr Ala Val Ser Glu Ala Ala Ala His Lys Tyr Gly Ile Asp Trp
                260                 265                 270

Ala Ser Gly Arg Gly Val Gly His Pro Tyr Arg Arg Val Arg Met
                275                 280                 285

Met Leu Arg
        288
```

(2) INFORMATION FOR SEQ ID NO:5:

(i) SEQUENCE CHARACTERISTICS:
        (A) LENGTH: 2042 base pairs
        (B) TYPE: Nucleic Acid
        (C) STRANDEDNESS: Single
        (D) TOPOLOGY: Linear (xi) SEQUENCE DESCRIPTION: SEQ ID NO:5:

-continued

```
GCGGACGCGT GGGTGAAATT GAAAATCAAG ATAAAAATGT TCACAATTAA        50
GCTCCTTCTT TTTATTGTTC CTCTAGTTAT TTCCTCCAGA ATTGATCAAG       100
ACAATTCATC ATTTGATTCT CTATCTCCAG AGCCAAAATC AAGATTTGCT       150
ATGTTAGACG ATGTAAAAAT TTTAGCCAAT GGCCTCCTTC AGTTGGGACA       200
TGGTCTTAAA GACTTTGTCC ATAAGACGAA GGGCCAAATT AATGACATAT       250
TTCAAAAACT CAACATATTT GATCAGTCTT TTTATGATCT ATCGCTGCAA       300
ACCAGTGAAA TCAAAGAAGA AGAAAAGGAA CTGAGAAGAA CTACATATAA       350
ACTACAAGTC AAAAATGAAG AGGTAAAGAA TATGTCACTT GAACTCAACT       400
CAAAACTTGA AAGCCTCCTA GAAGAAAAAA TTCTACTTCA ACAAAAAGTG       450
AAATATTTAG AAGAGCAACT AACTAACTTA ATTCAAAATC AACCTGAAAC       500
TCCAGAACAC CCAGAAGTAA CTTCACTTAA AACTTTTGTA GAAAAACAAG       550
ATAATAGCAT CAAAGACCTT CTCCAGACCG TGGAAGACCA ATATAAACAA       600
TTAAACCAAC AGCATAGTCA AATAAAAGAA ATAGAAAATC AGCTCAGAAG       650
GACTAGTATT CAAGAACCCA CAGAAATTTC TCTATCTTCC AAGCCAAGAG       700
CACCAAGAAC TACTCCCTTT CTTCAGTTGA ATGAAATAAG AAATGTAAAA       750
CATGATGGCA TTCCTGCTGA ATGTACCACC ATTTATAACA GAGGTGAACA       800
TACAAGTGGC ATGTATGCCA TCAGACCCAG CAACTCTCAA GTTTTTCATG       850
TCTACTGTGA TGTTATATCA GGTAGTCCAT GGACATTAAT TCAACATCGA       900
ATAGATGGAT CACAAAACTT CAATGAAACG TGGGAGAACT ACAAATATGG       950
TTTTGGGAGG CTTGATGGAG AATTTTGGTT GGGCCTAGAG AAGATATACT      1000
CCATAGTGAA GCAATCTAAT TATGTTTTAC GAATTGAGTT GGAAGACTGG      1050
AAAGACAACA AACATTATAT TGAATATTCT TTTTACTTGG GAAATCACGA      1100
AACCAACTAT ACGCTACATC TAGTTGCGAT TACTGGCAAT GTCCCCAATG      1150
CAATCCCGGA AAACAAAGAT TTGGTGTTTT CTACTTGGGA TCACAAAGCA      1200
AAAGGACACT TCAACTGTCC AGAGGGTTAT TCAGGAGGCT GGTGGTGGCA      1250
TGATGAGTGT GGAGAAAACA ACCTAAATGG TAAATATAAC AAACCAAGAG      1300
CAAAATCTAA GCCAGAGAGG AGAAGAGGAT TATCTTGGAA GTCTCAAAAT      1350
GGAAGGTTAT ACTCTATAAA ATCAACCAAA ATGTTGATCC ATCCAACAGA      1400
TTCAGAAAGC TTTGAATGAA CTGAGGCAAT TTAAAGGCAT ATTTAACCAT      1450
TAACTCATTC CAAGTTAATG TGGTCTAATA ATCTGGTATA AATCCTTAAG      1500
AGAAAGCTTG AGAAATAGAT TTTTTTTATC TTAAAGTCAC TGTCTATTTA      1550
AGATTAAACA TACAATCACA TAACCTTAAA GAATACCGTT TACATTTCTC      1600
AATCAAAATT CTTATAATAC TATTTGTTTT AAATTTTGTG ATGTGGGAAT      1650
CAATTTTAGA TGGTCACAAT CTAGATTATA ATCAATAGGT GAACTTATTA      1700
AATAACTTTT CTAAATAAAA AATTTAGAGA CTTTTATTTT AAAAGGCATC      1750
ATATGAGCTA ATATCACAAC TTTCCCAGTT TAAAAAACTA GTACTCTTGT      1800
TAAAACTCTA AACTTGACTA AATACAGAGG ACTGGTAATT GTACAGTTCT      1850
TAAATGTTGT AGTATTAATT TCAAAACTAA AAATCGTCAG CACAGAGTAT      1900
GTGTAAAAAT CTGTAATACA AATTTTTAAA CTGATGCTTC ATTTTGCTAC      1950
AAAATAATTT GGAGTAAATG TTTGATATGA TTTATTTATG AAACCTAATG      2000
```

AAGCAGAATT AAATACTGTA TTAAAATAAG TTCGCTGTCT TT        2042

(2) INFORMATION FOR SEQ ID NO:6:

(i) SEQUENCE CHARACTERISTICS:
        (A) LENGTH: 460 amino acids
        (B) TYPE: Amino Acid
        (D) TOPOLOGY: Linear (xi) SEQUENCE DESCRIPTION: SEQ ID NO:6:

```
Met Phe Thr Ile Lys Leu Leu Leu Phe Ile Val Pro Leu Val Ile
 1               5                  10                  15

Ser Ser Arg Ile Asp Gln Asp Asn Ser Ser Phe Asp Ser Leu Ser
                20                  25                  30

Pro Glu Pro Lys Ser Arg Phe Ala Met Leu Asp Asp Val Lys Ile
                35                  40                  45

Leu Ala Asn Gly Leu Leu Gln Leu Gly His Gly Leu Lys Asp Phe
                50                  55                  60

Val His Lys Thr Lys Gly Gln Ile Asn Asp Ile Phe Gln Lys Leu
                65                  70                  75

Asn Ile Phe Asp Gln Ser Phe Tyr Asp Leu Ser Leu Gln Thr Ser
                80                  85                  90

Glu Ile Lys Glu Glu Glu Lys Glu Leu Arg Arg Thr Thr Tyr Lys
                95                 100                 105

Leu Gln Val Lys Asn Glu Glu Val Lys Asn Met Ser Leu Glu Leu
               110                 115                 120

Asn Ser Lys Leu Glu Ser Leu Leu Glu Glu Lys Ile Leu Leu Gln
               125                 130                 135

Gln Lys Val Lys Tyr Leu Glu Glu Gln Leu Thr Asn Leu Ile Gln
               140                 145                 150

Asn Gln Pro Glu Thr Pro Glu His Pro Glu Val Thr Ser Leu Lys
               155                 160                 165

Thr Phe Val Glu Lys Gln Asp Asn Ser Ile Lys Asp Leu Leu Gln
               170                 175                 180

Thr Val Glu Asp Gln Tyr Lys Gln Leu Asn Gln Gln His Ser Gln
               185                 190                 195

Ile Lys Glu Ile Glu Asn Gln Leu Arg Arg Thr Ser Ile Gln Glu
               200                 205                 210

Pro Thr Glu Ile Ser Leu Ser Ser Lys Pro Arg Ala Pro Arg Thr
               215                 220                 225

Thr Pro Phe Leu Gln Leu Asn Glu Ile Arg Asn Val Lys His Asp
               230                 235                 240

Gly Ile Pro Ala Glu Cys Thr Thr Ile Tyr Asn Arg Gly Glu His
               245                 250                 255

Thr Ser Gly Met Tyr Ala Ile Arg Pro Ser Asn Ser Gln Val Phe
               260                 265                 270

His Val Tyr Cys Asp Val Ile Ser Gly Ser Pro Trp Thr Leu Ile
               275                 280                 285

Gln His Arg Ile Asp Gly Ser Gln Asn Phe Asn Glu Thr Trp Glu
               290                 295                 300

Asn Tyr Lys Tyr Gly Phe Gly Arg Leu Asp Gly Glu Phe Trp Leu
               305                 310                 315

Gly Leu Glu Lys Ile Tyr Ser Ile Val Lys Gln Ser Asn Tyr Val
               320                 325                 330
```

```
Leu Arg Ile Glu Leu Glu Asp Trp Lys Asp Asn Lys His Tyr Ile
            335                 340                 345

Glu Tyr Ser Phe Tyr Leu Gly Asn His Glu Thr Asn Tyr Thr Leu
            350                 355                 360

His Leu Val Ala Ile Thr Gly Asn Val Pro Asn Ala Ile Pro Glu
            365                 370                 375

Asn Lys Asp Leu Val Phe Ser Thr Trp Asp His Lys Ala Lys Gly
            380                 385                 390

His Phe Asn Cys Pro Glu Gly Tyr Ser Gly Gly Trp Trp His
            395                 400                 405

Asp Glu Cys Gly Glu Asn Asn Leu Asn Gly Lys Tyr Asn Lys Pro
            410                 415                 420

Arg Ala Lys Ser Lys Pro Glu Arg Arg Arg Gly Leu Ser Trp Lys
            425                 430                 435

Ser Gln Asn Gly Arg Leu Tyr Ser Ile Lys Ser Thr Lys Met Leu
            440                 445                 450

Ile His Pro Thr Asp Ser Glu Ser Phe Glu
            455                 460

(2) INFORMATION FOR SEQ ID NO:7:

(i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO:7:

ATGAGGTGGC CAAGCCTGCC CGAAGAAAGA GGC                              33

(2) INFORMATION FOR SEQ ID NO:8:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (xi) SEQUENCE DESCRIPTION: SEQ ID NO:8:

CAACTGGCTG GGCCATCTCG GGCAGCCTCT TTCTTCGGG                        39

(2) INFORMATION FOR SEQ ID NO:9:

(i) SEQUENCE CHARACTERISTICS:
        (A) LENGTH: 24 base pairs
        (B) TYPE: Nucleic Acid
        (C) STRANDEDNESS: Single
        (D) TOPOLOGY: Linear (xi) SEQUENCE DESCRIPTION: SEQ ID NO:9:

CCCAGCCAGA ACTCGCCGTG GGGA                                        24

(2) INFORMATION FOR SEQ ID NO:10:

(i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO:10:

TGGTTGGCAA AGGCAAGGTG GCTGACGATC CGG                              33
```

(2) INFORMATION FOR SEQ ID NO:11:

(i) SEQUENCE CHARACTERISTICS:
        (A) LENGTH: 43 base pairs
        (B) TYPE: Nucleic Acid
        (C) STRANDEDNESS: Single
        (D) TOPOLOGY: Linear (xi) SEQUENCE DESCRIPTION: SEQ ID NO:11:

GTGGCCCTTA TCTCTCCTGT ACAGCTTCCG GATCGTCAGC CAC    43

(2) INFORMATION FOR SEQ ID NO:12:

(i) SEQUENCE CHARACTERISTICS:
        (A) LENGTH: 27 base pairs
        (B) TYPE: Nucleic Acid
        (C) STRANDEDNESS: Single
        (D) TOPOLOGY: Linear (xi) SEQUENCE DESCRIPTION: SEQ ID NO:12:

TCCATTCCCA CCTATGACGC TGACCCA    27

(2) INFORMATION FOR SEQ ID NO:13:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO:13:

CCACGTTGGC TTGAAATTGA    20

(2) INFORMATION FOR SEQ ID NO:14:

(i) SEQUENCE CHARACTERISTICS:
        (A) LENGTH: 50 base pairs
        (B) TYPE: Nucleic Acid
        (C) STRANDEDNESS: Single
        (D) TOPOLOGY: Linear (xi) SEQUENCE DESCRIPTION: SEQ ID NO:14:

CCTCCAGAAT TGATCAAGAC AATTCATGAT TTGATTCTCT ATCTCCAGAG    50

(2) INFORMATION FOR SEQ ID NO:15:

(i) SEQUENCE CHARACTERISTICS:
        (A) LENGTH: 19 base pairs
        (B) TYPE: Nucleic Acid
        (C) STRANDEDNESS: Single
        (D) TOPOLOGY: Linear (xi) SEQUENCE DESCRIPTION: SEQ ID NO:15:

TCGTCTAACA TAGCAAATC    19

TIE LIGAND HOMOLOGUES

FIELD OF THE INVENTION

The present invention concerns isolated nucleic acid molecules encoding novel TIE ligands, the TIE proteins encoded by such nucleic acid molecules, as well as methods and means for making and using such nucleic acid and protein molecules.

BACKGROUND ART

The abbreviations "TIE" or "tie" are acronyms, which stand for "tyrosine kinase containing Ig and EGF homology domains" and were coined to designate a new family of receptor tyrosine kinases which are almost exclusively expressed in vascular endothelial cells and early hemopoietic cells, and are characterized by the presence of an EGF-like domain, and extracellular folding units stabilized by intra-chain disulfide bonds, generally referred to as "immunoglobulin (IG)-like" folds. A tyrosine kinase homologous cDNA fragment from human leukemia cells (tie) was described by Partanen et al., *Proc. Natl. Acad. Sci. USA* 87, 8913–8917 (1990). The MRNA of this human "tie" receptor has been detected in all human fetal and mouse embryonic tissues, and has been reported to be localized in the cardiac and vascular endothelial cells. Korhonen et al., *Blood* 80, 2548–2555 (1992); PCT Application Publication No. WO 93/14124 (published Jul. 22, 1993). The rat homolog of human tie, referred to as "tie-1", was identified by Maisonpierre et al., *Oncogene* 8, 1631–1637 (1993)). Another tie receptor, designated "tie-2" was originally identified in rats (Dumont et al., *Oncogene* 8, 1293–1301 (1993)), while the human homolog of tie-2, referred to as "ork" was described in U.S. Pat. No. 5,447,860 (Ziegler). The murine homolog of tie-2 was originally termed "tek." The cloning of a mouse tie-2 receptor from a brain capillary cDNA library is disclosed in PCT Application Publication No. WO 95/13387 (published May 18, 1995). The TIE receptors are believed to be actively involved in angiogenesis, and may play a role in hemopoiesis as well.

The expression cloning of human TIE-2 ligands has been described in PCT Application Publication No. WO 96/11269 (published Apr. 18, 1996) and in U.S. Pat. No. 5,521,073 (published May 28, 1996). A vector designated as λgt10 encoding a TIE-2 ligand named "htie-2 ligand 1" or "hTL1" has been deposited under ATCC Accession No. 75928. A plasmid encoding another TIE-2 ligand designated "htie-2 2" or "hTL2" is available under ATCC Accession No. 75928. This second ligand has been described as an antagonist of the TAI-2 receptor. The identification of secreted human and mouse ligands for the TIE-2 receptor has been reported by Davis et al., *Cell* 87, 1161–1169 (1996). The human ligand designated "Angiopoietin-1", to reflect its role in angiogenesis and potential action during hemopoiesis, is the same ligand as the ligand variously designated as "htie-2 1" or "hTL-1" in WO 96/11269. Angiopoietin-1 has been described to play an angiogenic role later and distinct from that of VEGF (Suri et al., *Cell* 87, 1171–1180 (1996)). Since TIE-2 is apparently upregulated during the pathologic angiogenesis requisite for tumor growth (Kaipainen et al., *Cancer Res.* 54, 6571–6577 (1994)) angiopoietin-1 has been suggested to be additionally useful for specifically targeting tumor vasculature (Davis et al., supra).

SUMMARY OF THE INVENTION

The present invention concerns novel human TIE ligand homologues with powerful effects on vasculature. The invention also provides for isolated nucleic acid molecules encoding such ligands or functional derivatives thereof, and vectors containing such nucleic acid molecules. The invention further concerns host cells transformed with such nucleic acid to produce the novel TIE ligands or functional derivatives thereof. The novel ligands may be agonists or antagonists of TIE receptors, known or hereinafter discovered. Their therapeutic or diagnostic use, including the delivery of other therapeutic or diagnostic agents to cells expressing the respective TIE receptors, is also within the scope of the present invention.

The present invention further provides for agonist or antagonist antibodies specifically binding the TIE ligands homologues herein, and the diagnostic or therapeutic use of such antibodies.

In another aspect, the invention concerns compositions comprising the novel ligands or antibodies.

In a further aspect, the invention concerns conjugates of the novel TIE ligands homologues of the present invention with other therapeutic or cytotoxic agents, and compositions comprising such conjugates. Because the TIE-2 receptor has been reported to be upregulated during the pathologic angiogenesis that is requisite for tumor growth, the conjugates of the TIE ligands homologues of the present invention to cytotoxic or other anti-tumor agents are useful in specifically targeting tumor vasculature.

In yet another aspect, the invention concerns a method for identifying a cell that expresses a TIE (e.g. TIE-2) receptor, which comprises contacting a cell with a detectably labeled TIE ligand homologue of the present invention under conditions permitting the binding of such TIE ligand homologue to the TIE receptor, and determining whether such binding has indeed occurred.

In a different aspect, the invention concerns a method for measuring the amount of a TIE ligand homologue of the present invention in a biological sample by contacting the biological sample with at least one antibody specifically binding the TIE ligand homologue, and measuring the amount of the TIE ligand homologue-antibody complex formed.

The invention further concerns a screening method for identifying polypeptide or small molecule agonists or antagonists of a TIE receptor based upon their ability to compete with a native or variant TIE ligand homologue of the present invention for binding to a corresponding TIE receptor.

The invention also concerns a method for imaging the presence of angiogenesis in wound healing, in inflammation or in tumors of human patients, which comprises administering detectably labeled TIE ligands homologues or agonist antibodies of the present invention, and detecting angiogenesis.

In another aspect, the invention concerns a method of promoting or inhibiting neovascularization in a patient by administering an effective amount of a TIE ligand homologue of the present invention in a pharmaceutically acceptable vehicle. In a preferred embodiment, the present invention concerns a method for the promotion of wound healing. In another embodiment, the invention concerns a method for promoting angiogenic processes, such as for inducing collateral vascularization in an ischemic heart or limb. In a further preferred embodiment, the invention concerns a method for inhibiting tumor growth.

In yet another aspect, the invention concerns a method of promoting bone development and/or maturation and/or growth in a patient, comprising administering to the patient an effective amount of a TIE ligand homologue of the present invention in a pharmaceutically acceptable vehicle.

In a further aspect, the invention concerns a method of promoting muscle growth and development, which comprises administering a patient in need an effective amount of a TIE ligand homologue of the present invention in a pharmaceutically acceptable vehicle.

The TIE ligands homologues of the present invention may be administered alone, or in combination with each other and/or with other therapeutic or diagnostic agents, including members of the VEGF family. Combinations therapies may lead to new approaches for promoting or inhibiting neovascularization, and muscle growth and development.

BRIEF DESCRIPTION OF THE FIGURES

FIGS. 2A–B are the nucleotide sequence of the TIE ligand homologue NL2 (SEQ. ID. NO: 1) (DNA 22780).

FIGS. 3A–B are the amino acid sequence of the TIE ligand homologue NL2 (SEQ. ID. NO:2).

FIG. 4 is the nucleotide sequence of the TIE ligand homologue NL3 (SEQ. ID. NO: 3) (DNA 33457).

FIG. 5 is the amino acid sequence of the TIE ligand homologue NL3 (SEQ. ID. NO: 4).

FIGS. 6A–B are the nucleotide sequence of the TIE ligand homologue FLS139 (SEQ. ID NO: 5) (DNA 16451).

FIGS. 7A–B are the amino acid sequence of the TIE ligand homologue FLS139 (SEQ. ID NO:6).

DETAILED DESCRIPTION OF THE INVENTION

A. TIE LIGANDS AND NUCLEIC ACID MOLECULES ENCODING THEM

Figure 1:
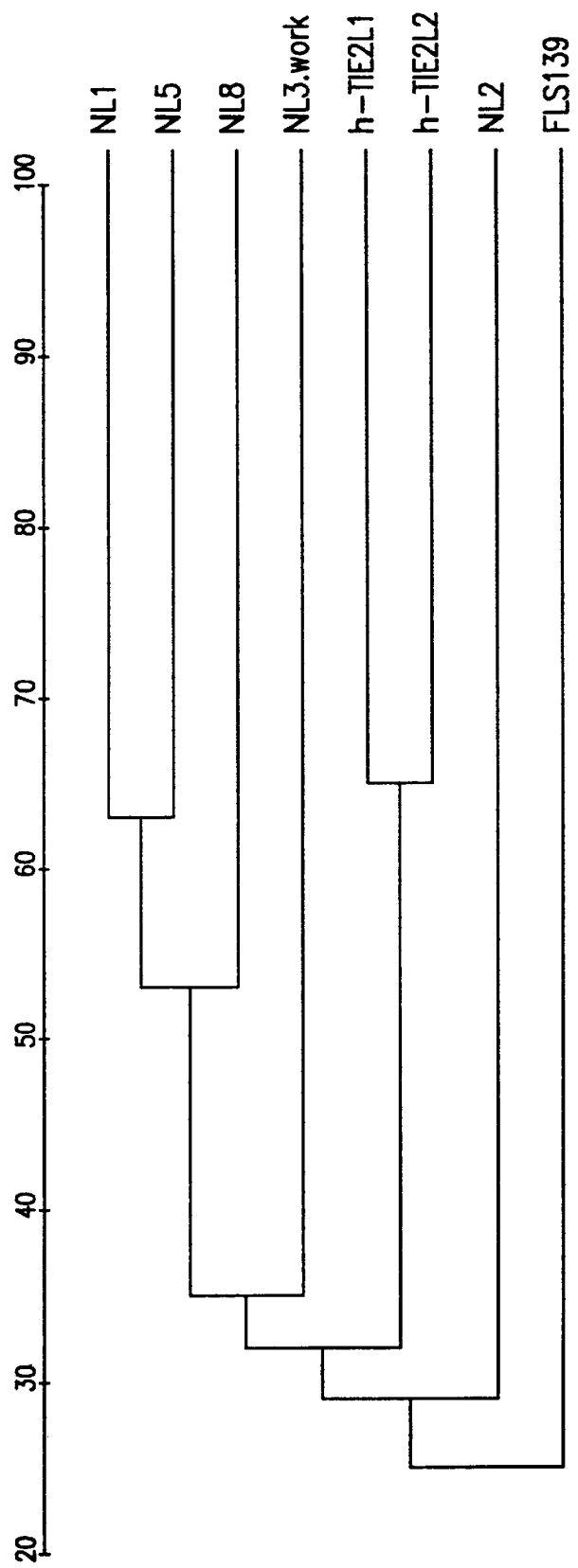
FIG. 1 is a graphic depiction of the relationship of the ligands NL2, NL3 and FLS139 with the two known ligands of the TIE2 receptor (h-TIE2L1 and h-TIE2L2) and with other TIE ligands homologues disclosed in application Ser. No. 08/933,821 filed at equal date.

The TIE ligands homologues of the present invention include the native human ligands designated NL2 (SEQ. ID. NO: 2), NL3 (SEQ. ID. NO: 4), and FLS139 (SEQ. ID. NO: 6), their homologs in other, non-human mammalian species, including, but not limited to, higher mammals, such as monkey; rodents, such as mice, rats, hamster; porcine; equine; bovine; naturally occurring allelic and splice variants, and biologically active (functional) derivatives, such as, amino acid sequence variants of such native molecules, as long as they differ from a native TL-1 or TL-2 ligand. Native NL2, as disclosed herein, has 27% amino acid sequence identity with hTL-1 (TIE2L1) and about 24% amino acid sequence identity with hTL-2 (T1E2L2). The amino acid sequence of native NL3, as disclosed herein, is about 30% identical with that of hTL-1 and about 29% identical with that of hTL-2. The amino acid sequence identity between native FLS139, as disclosed herein, and hTL-1 and h-TL2 is about 21%. The native TIE ligands homologues of the present invention are substantially free of other proteins with which they are associated in their native environment. This definition is not limited in any way by the method(s) by which the TIE ligands homologues of the present invention are obtained, and includes all ligands otherwise within the definition, whether purified from natural source, obtained by recombinant DNA technology, synthesized, or prepared by any combination of these and/or other techniques. The amino acid sequence variants of the native TIE ligands homologues of the present invention shall have at least about 90%, preferably, at least about 95%, more preferably at least about 98%, most preferably at least about 99% sequence identity with a full-length, native human TIE ligand homologue of the present invention, or with the fibrinogen-like domain of a native human TIE ligand homologue of the present invention. Such amino acid sequence variants preferably exhibit or inhibit a qualitative biological activity of a native TIE ligand homologue.

The term "fibrinogen domain" or "fibrinogen-like domain" is used to refer to amino acids from about position 278 to about position 498 in the known hTL-1 amino acid sequence; amino acids from about position 276 to about position 496 in the known hTL-2 amino acid sequence; amino acids from about position 180 to about 453 in the amino acid sequence of NL2; amino acids from about position 77 to about position 288 in the amino acid sequence of NL3; and amino acids from about position 238 to about position 460 in the amino acid sequence of FLS139, and to homologous domains in other TIE ligands homologues. The fibrinogen-like domain of NL2 is about 37–38% identical to that of the hTL-1 (TIE2L1) and hTL-2 (TIE2L2). The NL3 fibrinogen-like domain is about 37% identical to the fibrinogen-like domains of hTL-1 and hTL-2, while the FLS139 fibrinogen-like domain is about 32–33% identical to the fibrinogen-like domains of hTL-1 and hTL-2.

The term "nucleic acid molecule" includes RNA, DNA and cDNA molecules. It will be understood that, as a result of the degeneracy of the genetic code, a multitude of nucleotide sequences encoding a given TIE ligand homologue may be produced. The present invention specifically contemplates every possible variation of nucleotide sequences, encoding the TIE ligands homologues of the present invention, based upon all possible codon choices. Although nucleic acid molecules which encode the TIE ligands homologues herein are preferably capable of hybridizing, under stringent conditions, to a naturally occurring TIE ligand gene, it may be advantageous to produce nucleotide sequences encoding TIE ligands homologues, which possess a substantially different codon usage. For example, codons may be selected to increase the rate at which expression of the polypeptide occurs in a particular prokaryotic or eukaryotic host cells, in accordance with the frequency with which a particular codon is utilized by the host. In addition, RNA transcripts with improved properties, e.g. half-life can be produced by proper choice of the nucleotide sequences encoding a given TIE ligand homologue.

"Sequence identity" shall be determined by aligning the two sequences to be compared following the Clustal method of multiple sequence alignment (Higgins et al., *Comput. Appl. Biosci.* 5, 151–153 (1989), and Higgins et al., *Gene* 73, 237–244 (1988)) that is incorporated in version 1.6 of the Lasergene biocomputing software (DNASTAR, Inc., Madison, Wis.), or any updated version or equivalent of this software.

The terms "biological activity" and "biologically active" with regard to a TIE ligand homologue of the present invention refer to the ability of a molecule to specifically bind to and signal through a native TIE receptor, e. g. a native TIE-2 receptor, or to block the ability of a native TIE receptor (e.g. TIE-2) to participate in signal transduction. Thus, the (native and variant) TIE ligands homologues of the present invention include agonists and antagonists of a native TIE, e.g. TIE-2, receptor. Preferred biological activities of the TIE ligands homologues of the present invention include the ability to induce or inhibit vascularization. The ability to induce vascularization will be useful for the treatment of biological conditions and diseases, where vascularization is desirable, such as wound healing, ischaemia, and diabetes. On the other hand, the ability to inhibit or block vascularization may, for example, be useful in preventing or attenuating tumor growth. Another preferred biological activity is the ability to affect muscle growth or development. A further preferred biological activity is the ability to influence bone development, maturation, or growth.

The term "functional derivative" is used to define biologically active amino acid sequence variants of the native TIE ligands homologues of the present invention, as well as covalent modifications, including derivatives obtained by reaction with organic derivatizing agents, post-translational modifications, derivatives with nonproteinaceous polymers, and immunoadhesins.

The term "isolated" when used to describe the various polypeptides described herein, means polypeptides that have been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the TIE ligand's natural environment will not be present. Ordinarily, however, isolated polypeptide will be prepared by at least one purification step.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes nucleic acid molecules contained in cells that ordinarily express an TIE ligand of the present invention, where, for example, the nucleic acid molecule is in a chromosomal location different from that of natural cells.

The term "amino acid sequence variant" refers to molecules with some differences in their amino acid sequences as compared to a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule. Deletional variants include those having C- and/or N-terminal deletions (truncations) as well as variants with internal deletions of one or more amino acids. The preferred deletional variants of the present invention contain deletions outside the fibrinogen-like domain of a native TIE ligand of the present invention.

The amino acid sequence variants of the present invention may contain various combinations of amino acid substitutions, insertions and/or deletions, to produce molecules with optimal characteristics.

The amino acids may be classified according to the chemical composition and properties of their side chains. They are broadly classified into two groups, charged and uncharged. Each of these groups is divided into subgroups to classify the amino acids more accurately.

I. Charged Amino Acids
   Acidic Residues: aspartic acid, glutamic acid
   Basic Residues: lysine, arginine, histidine II. Uncharged Amino Acids
   Hydrophilic Residues: serine, threonine, asparagine, glutamine
   Aliphatic Residues: glycine, alanine, valine, leucine, isoleucine
   Non-polar Residues: cysteine, methionine, proline
   Aromatic Residues: phenylalanine, tyrosine, tryptophan Conservative substitutions involve exchanging a member within one group for another member within the same group, whereas non-conservative substitutions will entail exchanging a member of one of these classes for another. Variants obtained by non-conservative substitutions are expected to result in significant changes in the biological properties/function of the obtained variant Amino acid sequence deletions generally range from about 1 to 30 residues, more preferably about 1 to 10 residues, and typically are contiguous. Deletions may be introduced into regions not directly involved in the interaction with a native TIE receptor. Deletions are preferably performed outside the fibrinogen-like regions at the C-terminus of the TIE ligands homologues of the present invention.

Amino acid insertions include amino- and/or carboxyl-terminal fusions ranging in length from one residue to polypeptides containing a hundred or more residues, as well as intrasequence insertions of single or multiple amino acid residues. Intrasequence insertions (i.e. insertions within the TIE ligand homologue amino acid sequence) may range generally from about 1 to 10 residues, more preferably 1 to 5 residues, more preferably 1 to 3 residues. Examples of terminal insertions include the TIE ligands homologues with an N-terminal methionyl residue, an artifact of its direct expression in bacterial recombinant cell culture, and fusion of a heterologous N-terminal signal sequence to the N-terminus of the TIE ligand homologue molecule to facilitate the secretion of the mature TIE ligand homologue from recombinant host cells. Such signal sequences will generally be obtained from, and thus homologous to, the intended host cell species. Suitable sequences include, for example, STII or Ipp for E. coli, alpha factor for yeast, and viral signals such as herpes gD for mammalian cells. Other insertional variants of the native TIE ligand molecules include the fusion of the N- or C-terminus of the TIE ligand molecule to immunogenic polypeptides, e.g. bacterial polypeptides such as beta-lactamase or an enzyme encoded by the E. coli trp locus, or yeast protein, and C-terminal fusions with proteins having a long half-life such as immunoglobulin regions (preferably immunoglobulin constant regions), albumin, or ferritin, as described in WO 89/02922 published on Apr. 6, 1989.

Since it is often difficult to predict in advance the characteristics of a variant TIE ligand homologue, it will be appreciated that some screening will be needed to select the optimum variant.

Amino acid sequence variants of native TIE ligands homologues of the present invention are prepared by methods known in the art by introducing appropriate nucleotide changes into a native or variant TIE ligand homologue DNA, or by in vitro synthesis of the desired polypeptide. There are two principal variables in the construction of amino acid sequence variants: the location of the mutation site and the nature of the mutation. With the exception of naturally-occurring alleles, which do not require the manipulation of the DNA sequence encoding the TIE ligand homologue, the amino acid sequence variants of TIE are preferably constructed by mutating the DNA, either to arrive at an allele or an amino acid sequence variant that does not occur in nature.

One group of the mutations will be created within the domain or domains of the TIE ligands homologues of the present invention identified as being involved in the interaction with a TIE receptor, e.g. TIE-1 or TIE-2.

Alternatively or in addition, amino acid alterations can be made at sites that differ in TIE ligands homologues from various species, or in highly conserved regions, depending on the goal to be achieved.

Sites at such locations will typically be modified in series, e.g. by (1) substituting first with conservative choices and then with more radical selections depending upon the results achieved, (2) deleting the target residue or residues, or (3) inserting residues of the same or different class adjacent to the located site, or combinations of options 1–3.

One helpful technique is called "alanine scanning" (Cunningham and Wells, *Science* 244, 1081–1085 [1989]). Here, a residue or group of target residues is identified and substituted by alanine or polyalanine. Those domains demonstrating functional sensitivity to the alanine substitutions are then refined by introducing further or other substituents at or for the sites of alanine substitution.

After identifying the desired mutation(s), the gene encoding an amino acid sequence variant of a TIE ligand homologue can, for example, be obtained by chemical synthesis as hereinabove described.

More preferably, DNA encoding a TIE ligand homologue amino acid sequence variant is prepared by site-directed mutagenesis of DNA that encodes an earlier prepared variant or a nonvariant version of the ligand. Site-directed (site-specific) mutagenesis allows the production of ligand variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as, Edelman et al., *DNA* 2, 183 (1983). As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al, *Third Cleveland Symposium on Macromolecules and Recombinant DNA*, A. Walton, ed., Elsevier, Amsterdam (1981). This and other phage vectors are commercially available and their use is well known to those skilled in the art. A versatile and efficient procedure for the construction of oligodeoxyribonucleotide directed site-specific mutations in DNA fragments using M13-derived vectors was published by Zoller, M. J. and Smith, M., *Nucleic Acids Res.* 10, 6487–6500 [1982]). Also, plasmid vectors that contain a single-stranded phage origin of replication (Veira et al, *Meth. Enzymol.* 153, 3 [1987]) may be employed to obtain single-stranded DNA. Alternatively, nucleotide substitutions are introduced by synthesizing the appropriate DNA fragment in vitro, and amplifying it by PCR procedures known in the art.

In general, site-specific mutagenesis herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. USA* 75, 5765 (1978). This primer is then annealed with the single-stranded protein sequence-containing vector, and subjected to DNA-polymerizing enzymes such as, *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate host cells such as JP101 cells, and clones are selected that include recombinant vectors bearing the mutated sequence arrangement. Thereafter, the mutated region may be removed and placed in an appropriate expression vector for protein production.

The PCR technique may also be used in creating amino acid sequence variants of a TIE ligand. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more) part ligation.

In a specific example of PCR mutagenesis, template plasmid DNA (1 µg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp$^R$ kits (obtained from Perkin-Elmer Cetus, Norwalk, Conn. and Emeryville, Calif.), and 25 pmole of each oligonucleotide primer, to a final volume of 50 μl. The reaction mixture is overlayered with 35 μl mineral oil. The reaction is denatured for 5 minutes at 100° C., placed briefly on ice, and then 1 μl Thermus aguaticus (Taq) DNA polymerase (5 units/1), purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows:

2 min. 55° C.,
30 sec. 72° C., then 19 cycles of the following:
30 sec. 94° C.,
30 sec. 55° C., and
30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to appropriate treatments for insertion into a vector.

Another method for preparing variants, cassette mutagenesis, is based on the technique described by Wells et al [Gene 34, 315 (1985)]. The starting material is the plasmid (or vector) comprising the TIE ligand homologue DNA to be mutated. The codon(s) within the TIE ligand homologue to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the DNA encoding the TIE ligand homologue. After the restriction sites have been introduced into the plasmid, the plasmid is cut at these sites to linearize it. A double-stranded oligonucleotide encoding the sequence of the DNA between the restriction site but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated TIE ligand homologue DNA sequence.

Additionally, the so-called phagemid display method may be useful in making amino acid sequence variants of native or variant TIE ligands homologues. This method involves (a) constructing a replicable expression vector comprising a first gene encoding an receptor to be mutated, a second gene encoding at least a portion of a natural or wild-type phage coat protein wherein the first and second genes are heterologous, and a transcription regulatory element operably linked to the first and second genes, thereby forming a gene fusion encoding a fusion protein; (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; (f) contacting the phagemid particles with a suitable antigen so that at least a portion of the phagemid particles bind to the antigen; and (g) separating the phagemid particles that bind from those that do not. Steps (d) through (g) can be repeated one or more times. Preferably in this method the plasmid is under tight control of the transcription regulatory element, and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Most preferably, the amount is less than 20%. Typically in this method, the expression vector will further contain a secretory signal sequence fused to the DNA encoding each subunit of the polypeptide and the transcription regulatory element will be a promoter system. Preferred promoter systems are selected from lac Z, $\lambda_{PL}$, tac, T7 polymerase, tryptophan, and alkaline phosphatase promoters and combinations thereof. Also, normally the method will employ a helper phage selected from M13K07, M13R408, M13-VCS, and Phi X 174. The preferred helper phage is M13K07, and the preferred coat protein is the M13 Phage gene III coat protein. The preferred host is E. coli, and protease-deficient strains of E. coli.

Further details of the foregoing and similar mutagenesis techniques are found in general textbooks, such as, for example, Sambrook et al, Molecular Cloning: A laboratory Manual (New York: Cold Spring Harbor Laboratory Press, 1989), and Current Protocols in Molecular Biology, Ausubel et al, eds., Wiley-Interscience, 1991.

"Imunoadhesins" are chimeras which are traditionally constructed from a receptor sequence linked to an appropriate immunoglobulin constant domain sequence (immunoadhesins). Such structures are well known in the art. Immunoadhesins reported in the literature include fusions of the T cell receptor* [Gascoigne et al., Proc. Natl.Acad. Sci. USA 84, 2936–2940 (1987)]; CD4 [Capon et al, Nature 337, 525–531 (1989); Traunecker et al, Nature 339, 68–70 (1989); Zettmeissl et al, DNA Cell Biol. USA 9, 347–353 (1990); Bym et al, Nature 344, 667–670 (1990)]; L-selectin (homing receptor) [Watson et al, J. Cell. Biol. 110, 2221–2229 (1990); Watson et al, Nature 349, 164–167 (1991)]; CD44* [Aruffo et al, Cell 61, 1303–1313 (1990)]; CD28* and B7* [Linsley et al., J. Exp. Med. 173, 721–730 (1991)]; CTLA-4* [Lisley et al, J. Exp. Med. 174, 561–569 (1991)]; CD22* [Stamenkovic et al, Cell 66. 1133–1144 (1991)]; TNF receptor [Ashkenazi et al, Proc. Natl. Acad. Sci. USA 88, 10535–10539 (1991); Lesslauer et al., Eur. J. Immunol. 27, 2883–2886 (1991); Peppel et al, J. Exp. Med. 174, 1483–1489 (1991)]; NP receptors [Bennett et al, J. Biol. Chem. 266, 23060–23067 (1991)]; IgE receptor α-chain* [Ridgway and Gorman, J. Cell. Biol. 115, abstr. 1448 (1991)]; HGF receptor [Mark, M. R. et al., 1992, J. Biol. Chem. submitted], where the asterisk (*) indicates that the receptor is member of the immunoglobulin superfamily.

Ligand-immunoglobulin chimeras are also known, and are disclosed, for example, in U.S. Pat. Nos. 5,304,640 (for L-selectin ligands); 5,316,921 and 5,328,837 (for HGF variants). These chimeras can be made in a similar way to the construction of receptor-immunoglobulin chimeras.

Covalent modifications of the TIE ligands homologues of the present invention are included within the scope herein. Such modifications are traditionally introduced by reacting targeted amino acid residues of the TIE ligand homologue with an organic derivatizing agent that is capable of reacting with selected sides or terminal residues, or by harnessing mechanisms of post-translational modifications that function in selected recombinant host cells. The resultant covalent derivatives are useful in programs directed at identifying residues important for biological activity, for immunoassays, or for the preparation of anti-TIE ligand homologue antibodies for immunoaffinity purification of the recombinant. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R'—N=C=N—R') such as 1-cyclohexyl-3-(2-morpholinyl-4-ethyl) carbodiirnide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl, threonyl or tyrosyl residues, methylation of the α-amino groups of lysine, arginine, and histidine side chains (T. E. Creighton, *Proteins: Structure and Molecular Properties*, W.H. Freeman & Co., San Francisco, pp. 79–86 [1983]), acetylation of the N-terminal amine, and amidation of any C-terminal carboxyl group. The molecules may further be covalently linked to nonproteinaceous polymers, e.g. polyethylene glycol, polypropylene glycol or polyoxyalkylenes, in the manner set forth in U.S. Ser. No. 07/275,296 or U.S. Pat. Nos. 4,640,835; 4,496,689; 4,301,144; 4,670,417; 4,791,192 or 4,179,337.

Derivatization with bifunctional agents is useful for preparing intramolecular aggregates of the TIE ligand homologue with polypeptides as well as for cross-linking the TIE ligand polypeptide to a water insoluble support matrix or surface for use in assays or affinity purification. In addition, a study of interchain cross-links will provide direct information on conformational structure. Commonly used cross-linking agents include 1,1-bis(diazoacetyl)-2-phenylethane, glutaraldehyde, N-hydroxysuccinirnide esters, homobifunctional imidoesters, and bifunctional maleimides. Derivatizing agents such as methyl-3-[(p-azidophenyl)dithio] propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl, threonyl or tyrosyl residues, methylation of the α-amino groups of lysine, arginine, and histidine side chains [T. E. Creighton, *Proteins: Structure and Molecular Properties*, W.H. Freeman & Co., San Francisco, pp. 79–86 (1983)].

Other derivatives comprise the novel peptides of this invention covalently bonded to a nonproteinaceous polymer. The nonproteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol.

The TIE ligands homologues may be linked to various nonproteinaceous polymers, such as polyethylene glycol (PEG), polypropylene glycol or polyoxyalkylenes, in the manner set forth in U.S. Pat. Nos. 4,640,835; 4,496,689;

4,301,144; 4,670,417; 4,791,192 or 4,179,337. These variants, just as the immunoadhesins of the present invention are expected to have longer half-lives than the corresponding native TIE ligands homologues.

The TIE ligands homologues may be entrapped in microcapsules prepared, for example, by coacervation techniques or by interfacial polymerization, in colloidal drug delivery systems (e.g. liposomes, albumin microspheres, microemulsions, nano-particles and nanocapsules), or in macroemulsions. Such techniques are disclosed in *Remington's Pharmaceutical Sciences*, 16th Edition, Osol, A., Ed. (1980).

The term "native TIE receptor" is used herein to refer to a TIE receptor of any animal species, including, but not limited to, humans, other higher primates, e.g. monkeys, and rodents, e.g. rats and mice. The definition specifically includes the TIE-2 receptor, disclosed, for example, in PCT Application Serial No. WO 95/13387 (published May 18, 1995), and the endothelial cell receptor tyrosine kinase termed "TE" in PCT Application Publication No. WO 93/14124 (published Jul. 22, 1993), and preferably is TIE-2.

B. ANTI-TIE LIGAND HOMOLOGUE ANTIBODIES

The present invention covers agonist and antagonist antibodies, specifically binding the TIE ligands homologues. The antibodies may be monoclonal or polyclonal, and include, without limitation, mature antibodies, antibody fragments (e.g. Fab, F(ab')$_2$, F$_v$, etc.), single-chain antibodies and various chain combinations.

The term "antibody" is used in the broadest sense and specifically covers single monoclonal antibodies (including agonist, antagonist, and neutralizing antibodies) specifically binding a TIE ligand homologue of the present invention and antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-TIE ligand homologue antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. See, e.g. U.S. Pat. No. 4,816,567 and Mage et al., in *Monoclonal Antibody Production Techniques and Applications*, pp.79–97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature*, 256:495 (1975), or may be made by recombinant DNA methods such as described in U.S. Pat. No. 4,816,567. The "monoclonal antibodies" may also be isolated from phage libraries generated using the techniques described in McCafferty et al., *Nature*, 348:552–554 (1990), for example.

"Humanized" forms of non-human (e.g. murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

Polyclonal antibodies to a TIE ligand homologue of the present invention generally are raised in animals by multiple subcutaneous (sc) or intraperitoneal (ip) injections of the TIE ligand homologue and an adjuvant. It may be useful to conjugate the TIE ligand homologue or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, SOCl$_2$, or R$^1$N=C=NR, where R and R$^1$ are different alkyl groups.

Animals are immunized against the immunogenic conjugates or derivatives by combining 1 mg or 1 μg of conjugate (for rabbits or mice, respectively) with 3 volumes of Freud's complete adjuvant and injecting the solution intradermally at multiple sites. One month later the animals are boosted with ⅕ to ⅟₁₀ the original amount of conjugate in Freud's complete adjuvant by subcutaneous injection at multiple sites. 7 to 14 days later the animals are bled and the serum is assayed for anti-TIE ligand homologue antibody titer. Animals are boosted until the titer plateaus. Preferably, the animal boosted with the conjugate of the same TIE ligand homologue, but conjugated to a different protein and/or through a different cross-linking reagent. Conjugates also can be made in recombinant cell culture as protein fusions. Also, aggregating agents such as alum are used to enhance the immune response.

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the anti-TIE ligand homologue monoclonal antibodies of the invention may be made using the hybridoma method first described by Kohler & Milstein, Nature 256:495 (1975), or may be made by recombinant DNA methods [Cabilly, et al., U.S. Pat. No. 4,816,567].

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Goding, *Monoclonal Antibodies: Principles and Practice*, pp.59–103 (Academic Press, 1986)].

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies [Kozbor, J. Immunol. 133:3001 (1984); Brodeur, et al, *Monoclonal Antibody Production Techniques and Applications*, pp.51–63 (Marcel Dekker, Inc., New York, 1987)].

Culture medium in which hybridoma cells are growing is assayed for production of monoclonal antibodies directed against the TIE ligand homologue. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard, Anal. Biochem. 107:220 (1980).

After hybridoma cells are identified that produce antibodies of the desired specificity, affinity, and/or activity, the clones may be subcloned by limiting dilution procedures and grown by standard methods. Goding, *Monoclonal Antibodies: Principles and Practice*, pp.59–104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al, *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-TIE ligand homologue monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a TIE ligand homologue of the present invention and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; biotin; radioactive isotopic labels, such as, e.g., $^{125}I$, $^{32}P$, $^{14}C$, or $^3H$, or an enzyme, such as alkaline phosphatase, beta-galactosidase or horseradish peroxidase.

Any method known in the art for separately conjugating the antibody to the detectable moiety may be employed, including those methods described by Hunter, et al., *Nature* 144:945 (1962); David, et al., *Biochemistry* 13:1014 (1974); Pain, et al, *J. Immunol. Meth.* 40:219 (1981); and Nygren, *J. Histochem. and Cytochem.* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp.147–158 (CRC Press, Inc., 1987).

Competitive binding assays rely on the ability of a labeled standard (which may be a TIE ligand homologue or an immunologically reactive portion thereof) to compete with the test sample analyte (TIE ligand homologue) for binding with a limited amount of antibody. The amount of TIE ligand homologue in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat. No. 4,376, 110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al, *Nature* 321, 522–525 (1986); Riechmann et al, *Nature* 332 323–327 (1988); Verhoeyen et al, *Science* 239, 1534–1536 (1988)], by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed Aug. 21, 1992, which is a continuation-in-part of application Ser. No. 07/715,272 filed Jun. 14, 1991.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al, *Proc. Natl. Acad. Sci. USA* 90, 2551–255 (1993); Jakobovits et al., *Nature* 362, 255–258 (1993).

Bispecific antibodies are monoclonal, preferably human or humanized, antibodies that have binding specificities for at least two different antigens. In the present case, one of the binding specificities is for a particular TIE ligand, the other one is for any other antigen, and preferably for another ligand. For example, bispecific antibodies specifically binding two different TIE ligands homologues are within the scope of the present invention.

Methods for making bispecific antibodies are known in the art.

Traditionally, the recombinant production of bispecific antibodies is based on the coexpression of two immunoglobulin heavy chain-light chain pairs, where the two heavy chains have different specificities (Millstein and Cuello, *Nature* 305, 537–539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published May 13, 1993), and in Traunecker et al, *EMBO* 10, 3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, and second and third constant regions of an immunoglobulin heavy chain (CH2 and CH3). It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in copending application Ser. No. 07/931,811 filed Aug. 17, 1992.

For further details of generating bispecific antibodies see, for example, Suresh et al, *Methods in Enzymology* 121, 210 (1986).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

The term "agonist" is used to refer to peptide and non-peptide analogs of the native TIE ligands homologues of the present invention and to antibodies specifically binding such native TIE ligands homologues, provided that they have the ability to signal through a native TIE receptor (e.g. TIE-2). In other words, the term "agonist" is defined in the context of the biological role of the TIE receptor, and not in relation to the biological role of a native TIE ligand, which, as noted before, may be an agonist or antagonist of the TIE receptor biological function. Preferred agonists are promoters of vascularization.

The term "antagonist" is used to refer to peptide and non-peptide analogs of the native TIE ligands homologues of the present invention and to antibodies specifically binding such native TIE ligands homologues, provided that they have the ability to inhibit the biological function of a native TIE receptor (e.g. TIE-2). Again, the term "antagonist" is defined in the context of the biological role of the TIE receptor, and not in relation to the biological activity of a native TIE ligand homologue, which may be either an agonist or an antagonist of the TIE receptor biological function. Preferred antagonists are inhibitors of vasculogenesis.

C. CLONING AND EXPRESSION OF THE TIE LIGANDS

In the context of the present invention the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological property, as screened for in the originally transformed cell, are included.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

Expression and cloning vectors are well known in the art and contain a nucleic acid sequence that enables the vector to replicate in one or more selected host cells. The selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA of expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, the signal sequence may be a component of the vector, or it may be a part of the TIE ligand molecule that is inserted into the vector. If the signal sequence is heterologous, it should be selected such that it is recognized and processed (i.e. cleaved by a signal peptidase) by the host cell.

Heterologous signal sequences suitable for prokaryotic host cells are preferably prokaryotic signal sequences, such as the α-amylase, ompA, ompC, ompE, ompF, alkaline phosphatase, penicillinase, lpp, or heat-stable enterotoxin II leaders. For yeast secretion the yeast invertase, amylase, alpha factor, or acid phosphatase leaders may, for example, be used. In mammalian cell expression mammalian signal sequences are most suitable. The listed signal sequences are for illustration only, and do not limit the scope of the present invention in any way.

(ii) Origin of Replication Component

Both expression and cloning vectors contain a nucleic acid sequence that enabled the vector to replicate in one or more selected host cells. Generally, in cloning vectors this sequence is one that enables the vector to replicate independently of the host chromosomes, and includes origins of replication or autonomously replicating sequences. Such sequence are well known for a variety of bacteria, yeast and viruses. The origin of replication from the well-known plasmid pBR322 is suitable for most gram negative bacteria, the $2\mu$ plasmid origin for yeast and various viral origins (SV40, polyoma, adenovirus, VSV or BPV) are useful for cloning vectors in mammalian cells. Origins of replication are not needed for mammalian expression vectors (the SV40 origin may typically be used only because it contains the early promoter). Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA is also cloned by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the DNA encoding the desired heterologous polypeptide. However, the recovery of genomic DNA is more complex than that of an exogenously replicated vector because restriction enzyme digestion is required to excise the encoded polypeptide molecule.

(iii) Selection Gene Component

Expression and cloning vectors should contain a selection gene, also termed a selectable marker. This is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b)

complement auxotrophic deficiencies, or (c) supply critical nutrients not available from complex media, e.g. the gene encoding D-alanine racemase for bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin [Southern et al., *J. Molec. Appl. Genet.* 1, 327 (1982)], mycophenolic acid [Mulligan et al, *Science* 209, 1422 (1980)], or hygromycin [Sudgen et al, *Mol. Cel. Biol.* 5, 410–413 (1985)]. The three examples given above employ bacterial genes under eukaryotic control to convey resistance to the appropriate drug G418 or neomycin (geneticin), xgpt (mycophenolic acid), or hygromycin, respectively.

Other examples of suitable selectable markers for mammalian cells are dihydrofolate reductase (DHFR) or thymidine kinase. Such markers enable the identification of cells which were competent to take up the desired nucleic acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the desired polypeptide. Amplification is the process by which genes in greater demand for the production of a protein critical for growth are reiterated in tandem within the chromosomes of successive generations of recombinant cells. Increased quantities of the desired polypeptide are synthesized from the amplified DNA.

For example, cells transformed with the DHFR selection gene are first identified by culturing all of the transformants in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Nat'l. Acad. Sci. USA* 77, 4216 (1980). A particularly useful DHFR is a mutant DHFR that is highly resistant to MTX (EP 117,060). This selection agent can be used with any otherwise suitable host, e.g. ATCC No. CCL61 CHO-K1, notwithstanding the presence of endogenous DHFR. The DNA encoding DHFR and the desired polypeptide, respectively, then is amplified by exposure to an agent (methotrexate, or MTX) that inactivates the DHFR. One ensures that the cell requires more DHFR (and consequently amplifies all exogenous DNA) by selecting only for cells that can grow in successive rounds of evergreater MTX concentration. Alternatively, hosts co-transformed with genes encoding the desired polypeptide, wild-type DHFR, and another selectable marker such as the neo gene can be identified using a selection agent for the selectable marker such as G418 and then selected and amplified using methotrexate in a wild-type host that contains endogenous DHFR. (See also U.S. Pat. No. 4,965,199).

A suitable selection gene for use in yeast is the trp 1 gene present in the yeast plasmid YRp7 (Stinchcomb et al., 1979, *Nature* 282:39; Kingsman et al, 1979, *Gene* 7:141; or Tschemper et al., 1980, *Gene* 10: 157). The trp 1 gene provides a selection marker for a mutant strain of yeast lacking the ability to grow in tryptophan, for example, ATCC No. 44076 or PEP4-1 (Jones, 1977, *Genetics* 85:12). The presence of the trp 1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

(iv) Promoter Component

Expression vectors, unlike cloning vectors, should contain a promoter which is recognized by the host organism and is operably linked to the nucleic acid encoding the desired polypeptide. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the desired polypeptide by removing them from their gene of origin by restriction enzyme digestion, followed by insertion 5' to the start codon for the polypeptide to be expressed. This is not to say that the genomic promoter for a TIE ligand homologue is not usable. However, heterologous promoters generally will result in greater transcription and higher yields of expressed TIE ligands homologues as compared to the native TIE ligand homologues promoters.

Promoters suitable for use with prokaryotic hosts include the β-lactamase and lactose promoter systems (Chang et al., *Nature* 275:615 (1978); and Goeddel et al., *Nature* 281:544 (1979)), alkaline phosphatase, a tryptophan (trp) promoter system (Goeddel, *Nucleic Acids Res.* 8:4057 (1980) and EPO Appln. Publ. No. 36,776) and hybrid promoters such as the tac promoter (H. de Boer et al., *Proc. Nat'l. Acad. Sci. USA* 80:21–25 (1983)). However, other known bacterial promoters are suitable. Their nucleotide sequences have been published, thereby enabling a skilled worker operably to ligate them to DNA encoding a TIE ligand (Siebenlist et al., *Cell* 20:269 (1980)) using linkers or adaptors to supply any required restriction sites. Promoters for use in bacterial systems also will contain a Shine-Dalgarno (S.D.) sequence operably linked to the DNA encoding a TIE ligand.

Suitable promoting sequences for use with yeast hosts include the promoters for 3-phosphoglycerate kinase (Hitzeman et al. *J. Biol. Chem.* 255:2073 (1980)) or other glycolytic enzymes (Hess et al, *J. Adv. Enzyme Reg.* 7:149 (1978); and Holland, *Biochemistry* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

TIE ligand transcription from vectors in mammalian host cells may be controlled by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat shock promoters, and from the promoter normally associated with the TIE ligand sequence, provided such promoters are compatible with the host cell systems.

The early and late promoters of the SV40 virus are conveniently obtained as an SV40 restriction fragment which also contains the SV40 viral origin of replication [Fiers et al, *Nature* 273:113 (1978), Mulligan and Berg, *Science* 209, 1422–1427 (1980); Pavlakis et al, *Proc. Natl. Acad. Sci. USA* 78, 7398–7402 (1981)]. The immediate early promoter of the human cytomegalovirus is conveniently obtained as a HindIII E restriction fragment [Greenaway et al, *Gene* 18, 355–360 (1982)]. A system for expressing DNA in mammalian hosts using the bovine papilloma virus as a vector is disclosed in U.S. Pat. No. 4,419,446. A modification of this system is described in U.S. Pat. No. 4,601,978. See also, Gray et al, *Nature* 295, 503–508 (1982) on expressing cDNA encoding human immune interferon in monkey cells; Reyes et al., *Nature* 297, 598–601 (1982) on expressing human β-interferon cDNA in mouse cells under the control of a thymidine kinase promoter from herpes simplex virus; Canaani and Berg, *Proc. Natl. Acad. Sci. USA* 79, 5166–5170 (1982) on expression of the human interferon β1 gene in cultured mouse and rabbit cells; and Gorman et al, *Proc. Natl. Acad. Sci., USA* 79, 6777–6781 (1982) on expression of bacterial CAT sequences in CV-1 monkey kidney cells, chicken embryo fibroblasts, Chinese hamster ovary cells, HeLa cells, and mouse HIN-3T3 cells using the Rous sarcoma virus long terminal repeat as a promoter.

(v) Enhancer Element Component

Transcription of a DNA encoding the TIE ligands homologues of the present invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent having been found 5' [Laimins et al., *Proc. Natl. Acad. Sci. USA* 78, 993 (1981)] and 3' [Lasky et al., *Mol Cel. Biol.* 3, 1108 (1983)] to the transcription unit, within an intron [Banerji et al., *Cell* 33, 729 (1983)] as well as within the coding sequence itself [Osborne et al, *Mol. Cel. Biol.* 4, 1293 (1984)]. Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature* 297, 17–18 (1982) on enhancing elements for activation of eukaryotic promoters. The enhancer may be spliced into the vector at a position 5' or 3' to the TIE ligand DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the MRNA encoding the TIE ligand homologue. The 3' untranslated regions also include transcription termination sites.

Construction of suitable vectors containing one or more of the above listed components, the desired coding and control sequences, employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al, *Nucleic Acids Res.* 9, 309 (1981) or by the method of Maxam et al., *Methods in Enzymology* 65, 499 (1980).

Particularly useful in the practice of this invention are expression vectors that provide for the transient expression in mammalian cells of DNA encoding a TIE ligand homologue. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient systems, comprising a suitable expression vector and a host cell, allow for the convenient positive identification of polypeptides encoded by clones DNAs, as well as for the rapid screening of such polypeptides for desired biological or physiological properties. Thus, transient expression systems are particularly useful in the invention for purposes of identifying analogs and variants of a TIE ligand homologue.

Other methods, vectors, and host cells suitable for adaptation to the synthesis of the TIE polypeptides in recombinant vertebrate cell culture are described in Getting et al., *Nature* 293, 620–625 (1981); Mantel et al, *Nature* 281, 40–46 (1979); Levinson et al.; EP 117,060 and EP 117,058. A particularly useful plasmid for mammalian cell culture expression of the TIE ligand homologue polypeptides is pRK5 (EP 307,247), along with its derivatives, such as, pRK5D that has an sp6 transcription initiation site followed by an SfiI restriction enzyme site preceding the Xho/NotlI cDNA cloning sites, and pRK5B, a precursor of pRK5D that does not contain the SfiI site; see, Holmes et al., *Science* 253, 1278–1280 (1991).

(vii) Construction and Analysis of Vectors

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequences by the methods of Messing et al., *Nuclei Acids*

*Res.* 9, 309 (1981) or by the method of Maxam et al, *Methods in Enzymology* 65, 499 (1980).

(viii) Transient Expression Vectors

Particularly useful in the practice of this invention are expression vectors that provide for the transient expression in mammalian cells of DNA encoding a TIE ligand homologue. In general, transient expression involves the use of an expression vector that is able to replicate efficiently in a host cell, such that the host cell accumulates many copies of the expression vector and, in turn, synthesizes high level of a desired polypeptide encoded by the expression vector. Sambrook et al, supra, pp. 16.17–16.22. Transient expression systems, comprising a suitable expression vector and a host cell, allow for the convenient positive screening of such polypeptides for desired biological or physiological properties. Thus transient expression systems are particularly useful in the invention for purposes of identifying analogs and variants of native TIE ligands homologues with the requisite biological activity.

(ix) Suitable Exemplary Vertebrate Cell Vectors

Other methods, vectors, and host cells suitable for adaptation to the synthesis of a TIE ligand homologue (including functional derivatives of native proteins) in recombinant vertebrate cell culture are described in Gething et al, *Nature* 293, 620–625 (1981); Mantei et al, *Nature* 281, 40–46 (1979); Levinson et al, EP 117,060; and EP 117,058. A particularly useful plasmid for mammalian cell culture expression of a TIE ligand is pRK5 (EP 307,247) or pSVI6B (PCT Publication No. WO 91/08291).

Suitable host cells for cloning or expressing the vectors herein are the prokaryote, yeast or higher eukaryote cells described above. Suitable prokaryotes include gram negative or gram positive organisms, for example *E. coli* or bacilli. A preferred cloning host is *E. coli* 294 (ATCC 31,446) although other gram negative or gram positive prokaryotes such as *E. coli* B. *E. coli* X1776 (ATCC 31,537), *E. coli* W3110 (ATCC 27,325), Pseudomonas species, or *Serratia Marcesans* are suitable.

In addition to prokaryotes, eukaryotic microbes such as filamentous fungi or yeast are suitable hosts for vectors herein. *Saccharomvces cerevisiae*, or common baker's yeast, is the most commonly used among lower eukaryotic host microorganisms. However, a number of other genera, species and strains are commonly available and useful herein, such as *S. pombe* [Beach and Nurse, *Nature* 290, 140 (1981)], *Kluyveromyces lactis* [Louvencourt et al., *J. Bacteriol.* 737 (1983)]; yarrowia (EP 402,226); *Pichia pastoris* (EP 183,070), *Trichoderma reesia* (EP 244,234); *Neurospora crassa* [Case et al, *Proc. Natl. Acad. Sci. USA* 76, 5259–5263 (1979)]; and Aspergillus hosts such as *A. nidulans* [Ballance et al., *Biochem. Biophys. Res. Commun.* 112, 284–289 (1983); Tilburn et al., *Gene* 26, 205–221 (1983); Yelton et al, *Proc. Natl. Acad. Sci. USA* 81, 1470–1474 (1984)] and *A. niger* [Kelly and Hynes, *EMBO J.* 4, 475–479 (1985)].

Suitable host cells may also derive from multicellular organisms. Such host cells are capable of complex processing and glycosylation activities. In principle, any higher eukaryotic cell culture is workable, whether from vertebrate or invertebrate culture, although cells from mammals such as humans are preferred. Examples of invertebrate cells include plants and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melangaster* (fruitfly), and *Bombyx mori* host cells have been identified. See, e.g. Luckow et al., *Bio/Technology* 6, 47–55 (1988); Miller et al, in *Genetic Engineering*, Setlow, J. K. et al., eds., Vol. 8 (Plenum Publishing, 1986), pp. 277–279; and Maeda et al., *Nature* 315, 592–594 (1985). A variety of such viral strains are publicly available, e.g. the L-1 variant of *Autographa californica* NPV, and such viruses may be used as the virus herein according to the present invention, particularly for transfection of *Spodoptera frugiperda* cells.

Generally, plant cells are transfected by incubation with certain strains of the bacterium *Agrobacterium tumefaciens*, which has been previously manipulated to contain the TIE ligand homologue DNA. During incubation of the plant cell culture with *A. tumefaciens*, the DNA encoding a TIE ligand homologue is transferred to the plant cell host such that it is transfected, and will, under appropriate conditions, express the TIE ligand homologue DNA. In addition, regulatory and signal sequences compatible with plant cells are available, such as the nopaline synthase promoter and polyadenylation signal sequences. Depicker et al., *J. Mol. Appl. Gen.* 1, 561 (1982). In addition, DNA segments isolated from the upstream region of the T-DNA 780 gene are capable of activating or increasing transcription levels of plant-expressible genes in recombinant DNA-containing plant tissue. See EP 321,196 published Jun. 21, 1989.

However, interest has been greatest in vertebrate cells, and propagation of vertebrate cells in culture (tissue culture) is per se well known. See *Tissue Culture*, Academic Press, Kruse and Patterson, editors (1973). Examples of useful mammalian host cell lines are monkey kidney CV1 line transformed by SV40 (COS-7, ATCC CRL 1651); human embryonic kidney cell line [293 or 293 cells subeloned for growth in suspension culture, Graham et al, *J. Gen. Virol.* 36, 59 (1977)]; baby hamster kidney cells 9BHK, ATCC CCL 10); Chinese hamster ovary cells/-DHFR [CHO, Urlaub and Chasin, *Proc. Natl. Acad. Sci. USA* 77, 4216 (1980)]; mouse sertolli cells [TM4, Mather, *Biol. Reprod.* 23, 243–251 (1980)]; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL75); human liver cells (Hep G2, HB 8065); mouse mammary tumor (MMT 060562, ATCC CCL51); TRI cells [Mather et al, *Annals N.Y. Acad. Sci.* 383 44068 (1982)]; MRC 5 cells; FS4 cells; and a human hepatoma cell line (Hep G2). Preferred host cells are human embryonic kidney 293 and Chinese hamster ovary cells.

Particularly preferred host cells for the purpose of the present invention are vertebrate cells producing the TIE ligands homologues of the present invention.

Host cells are transfected and preferably transformed with the above-described expression or cloning vectors and cultured in conventional nutrient media modified as is appropriate for inducing promoters or selecting transformants containing amplified genes.

Prokaryotes cells used to produced the TIE ligands homologues of this invention are cultured in suitable media as describe generally in Sambrook et al., supra.

Mammalian cells can be cultured in a variety of media Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham and Wallace, *Meth. Enzymol.* 58, 44 (1979); Bames and Sato, *Anal. Biochem.* 102, 255 (1980), U.S. Pat. No. 4,767,704; 4,657, 866; 4,927,762; or 4,560,655; WO 90/03430; WO 87/00195 or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug) trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH and the like, suitably are those previously used with the host cell selected for cloning or expression, as the case may be, and will be apparent to the ordinary artisan.

The host cells referred to in this disclosure encompass cells in in vitro cell culture as well as cells that are within a host animal or plant.

It is further envisioned that the TIE ligands homologues of this invention may be produced by homologous recombination, or with recombinant production methods utilizing control elements introduced into cells already containing DNA encoding the particular TIE ligand homologue.

Gene amplification and/or expression may be measured in a sample directly, for example, by conventional Southern blotting, Northern blotting to quantitate the transcription of mRNA [Thomas, *Proc. Natl. Acad. Sci. USA* 77, 5201–5205 (1980)], dot blotting (DNA analysis), or in situ hybridization, using an appropriately labeled probe, based on the sequences provided herein. Various labels may be employed, most commonly radioisotopes, particularly $^{32}$P. However, other techniques may also be employed, such as using biotin-modified nucleotides for introduction into a polynucleotide. The biotin then serves as a site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to the surface, so that upon the fonnation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hse et al, *Am. J. Clin. Pharm.* 75 734–738 (1980).

Antibodies useful for immunohistochemical staining and-lor assay of sample fluids may be either monoclonal or polyclonal, and may be prepared in any animal. Conveniently, the antibodies may be prepared against a native TIE ligand homologue polypeptide of the present invention, or against a synthetic peptide based on the DNA sequence provided herein as described further hereinbelow.

The TIE ligand homologue may be produced in host cells in the form of inclusion bodies or secreted into the periplasmic space or the culture medium, and is typically recovered from host cell lysates. The recombinant ligands may be purified by any technique allowing for the subsequent formation of a stable protein.

When the TIE ligand homologue is expressed in a recombinant cell other than one of human origin, it is completely free of proteins or polypeptides of human origin. However, it is necessary to purify the TIE ligand homologue from recombinant cell proteins or polypeptides to obtain preparations that are substantially homogenous as to the ligand. As a first step, the culture medium or lysate is centrifuged to remove particulate cell debris. The membrane and soluble protein fractions are then separated. The TIE ligand homologue may then be purified from the soluble protein fraction. The following procedures are exemplary of suitable purification procedures: fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; and protein A Sepharose columns to remove contaminants such as IgG.

Functional derivatives of the TIE ligands homologues in which residues have been deleted, inserted and/or substituted are recovered in the same fashion as the native ligands, taking into account of any substantial changes in properties occasioned by the alteration. For example, fusion of the TIE ligand homologue with another protein or polypeptide, e.g. a bacterial or viral antigen, facilitates purification; an immunoaffinity column containing antibody to the antigen can be used to absorb the fusion. Immunoaffinity columns such as a rabbit polyclonal anti-TIE ligand homologue column can be employed to absorb TIE ligand variants by binding to at least one remaining immune epitope. A protease inhibitor, such as phenyl methyl sulfonyl fluoride (PMSF) also may be useful to inhibit proteolytic degradation during purification, and antibiotics may be included to prevent the growth of adventitious contaminants. The TIE ligands homologue of the present invention are conveniently purified by affinity chromatography, based upon their ability to bind to a TIE receptor, e.g. TIE-2.

One skilled in the art will appreciate that purification methods suitable for native TIE ligands homologue may require modification to account for changes in the character of a native TIE ligand homologue or its variants upon expression in recombinant cell culture

D. USE OF THE TIE LIGANDS, NUCLEIC ACID MOLECULES AND ANTIBODIES

The TIE ligands homologues of the present invention are useful in promoting the survival and/or growth and/or differentiation of TIE receptor (e.g. TIE-2 receptor) expressing cells in cell culture.

The TIE ligands homologues may be additionally used to identify cells which express native TIE receptors, e.g. the TIE-2 receptor. To this end, a detectably labeled ligand is contacted with a target cell under condition permitting its binding to the TIE receptor, and the binding is monitored.

The TIE ligands homologues herein may also be used to identify molecules exhibiting a biological activity of a TIE ligand homologue, for example, by exposing a cell expressing a TIE ligand herein to a test molecule, and detecting the specific binding of the test molecule to a TIE (e.g. TIE-2) receptor, either by direct detection, or base upon secondary biological effects. This approach is particularly suitable for identifying new members of the TIE ligand homologue family, or for screening peptide or non-peptide small molecule libraries.

The TIE ligands homologues disclosed herein are also useful in screening assays designed to identify agonists or antagonists of a native TIE (e.g. TIE-2) receptor, which promote or inhibit angiogenesis, and/or play an important role in muscle growth or development and/or bone development, maturation or growth. For example, antagonists of the TIE-2 receptor may be identified based upon their ability to block the binding of a TIE ligand homologue of the present invention to a native TIE receptor, as measured, for example, by using BiAcore biosensor technology (BIAcore; Pharmacia Biosensor, Midscataway, N.J.); or by monitoring their ability to block the biological response caused by a biologically active TIE ligand homologue herein. Biological responses that may be monitored include, for example, the phosphorylation of the TIE-2 receptor or downstream components of the TIE-2 signal transduction pathway, or survival, growth or differentiation of cells expressing the TIE-2 receptor. Cell-based assays, utilizing cells that do not normally the TIE-2 receptor, engineered to express this receptor, or to coexpress the TIE-2 receptor and a TIE ligand homologue of the present invention, are particularly convenient to use.

In a particular embodiment, small molecule agonists and antagonists of a native TIE receptor, e.g. the TIE-2 receptor, can be identified, based upon their ability to interfere with the TIE ligand/TIE receptor interaction. There are numerous ways for measuring the specific binding of a test molecule to a TIE receptor, including, but not limited to detecting or measuring the amount of a test molecule bound to the surface of intact cells expressing the TIE receptor, cross-linked to the TIE receptor in cell lysates, or bound to the TIE receptor in vitro.

Detectably labeled TIE ligands homologues include, for example, TIE ligands homologues covalently or non-covalently linked to a radioactive substances, e.g. $^{125}I$, a fluorescent substance, a substance having enzymatic activity (preferably suitable for calorimetric detection), a substrate for an enzyme (preferably suitable for calorimetric detection), or a substance that can be recognized by a(n) (detectably labeled) antibody molecule.

The assays of the present invention may be performed in a manner similar to that described in PCT Publication WO 96/11269, published Apr. 18, 1996.

The TIE ligands of the present invention are also useful for purifying TIE receptors, e.g. TIE-2 receptors, optionally used in the form of imrnmunoadhesins, in which the TIE ligand homologue or the TIE receptor binding portion thereof is fused to an immunoglobulin heavy or light chain constant region.

The nucleic acid molecules of the present invention are useful for detecting the expression of TIE ligands homologues in cells or tissue sections. Cells or tissue sections may be contacted with a detectably labeled nucleic acid molecule encoding a TIE ligand of the present invention under hybridizing conditions, and the presence of mRNA hybridized to the nucleic acid molecule determined, thereby detecting the expression of the TIE ligand homologue.

Antibodies of the present invention may, for example, be used in immunoassays to measure the amount of a TIE ligand in a biological sample. The biological sample is contacted with an antibody or antibody mixture specifically binding the a TIE ligand homologue of the present invention, and the amount of the complex formed with a ligand present in the test sample is measured.

Antibodies to the TIE ligands homologues herein may additionally be used for the delivery of cytotoxic molecules, e.g. radioisotopes or toxins, or therapeutic agents to cells expressing a corresponding TIE receptor. The therapeutic agents may, for example, be other TIE ligands homologues, including the TIE-2 ligand, members of the vascular endothelial growth factor (VEGF) family, or known anti-tumor agents, and agents known to be associated with muscle growth or development, or bone development, maturation, or growth.

Anti-TIE ligand homologue antibodies are also suitable as diagnostic agents, to detect disease states associated with the expression of a TIE (e.g. TIE-2) receptor. Thus, detectably labeled TIE ligands and antibody agonists of a TIE receptor can be used for imaging the presence of antiogenesis.

In addition, the new TIE ligands homologues herein can be used to promote neovascularization, and may be useful for inhibiting tumor growth.

Further potential therapeutic uses include the modulation of muscle and bone development, maturation, or growth.

For therapeutic use, the TIE ligands homologues or anti-TIE ligand homologue antibodies of the present invention are formulated as therapeutic composition comprising the active ingredient(s) in admixture with a pharmacologically acceptable vehicle, suitable for systemic or topical application. The pharmaceutical compositions of the present invention are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules) or in macroemulsions. Such techniques are disclosed in *Remington's Pharmaceutical Sciences*, supra.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Suitable examples of sustained release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (U. Sidman et al, 1983, "Biopolymers" 22 (1): 547–556), poly (2-hydroxyethyl-methacrylate) (R. Langer, et al, 1981, "J. Biomed. Mater. Res." 15: 167–277 and R. Langer, 1982, Chem. Tech." 12: 98–105), ethylene vinyl acetate (R. Langer et al., Id.) or poly-D-(-)-3-hydroxybutyric acid (EP 133, 988A). Sustained release compositions also include liposomes. Liposomes containing a molecule within the scope of the present invention are prepared by methods known per se: DE 3,218,121A; Epstein et al., 1985, "Proc. Natl. Acad. Sci. USA" 82: 3688–3692; Hwang et al., 1980, "Proc. Natl. Acad. Sci. USA" 77: 4030–4034; EP 52322A; EP 36676A; EP 88046A; EP 143949A; EP 142641A; Japanese patent application 83–118008; U.S. Pat. Nos. 4,485,045 and 4,544, 545; and EP 102,324A. Ordinarily the liposomes are of the small (about 200–800 Angstroms) unilamelar type in which the lipid content is greater than about 30 mol. % cholesterol, the selected proportion being adjusted for the optimal NT-4 therapy.

An effective amount of a molecule of the present invention to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 $\mu$g/kg to up to 100 mg/kg or more, depending on the factors mentioned above. Typically, the clinician will administer a molecule of the present invention until a dosage is reached that provides the required biological effect. The progress of this therapy is easily monitored by conventional assays.

Further details of the invention will be apparent from the following non-limiting examples.

EXAMPLE 1

Identification of the FLS139 Ligand

FLS139 was identified in a cDNA library prepared from human fetal liver mRNA obtained from Clontech Laboratories, Inc. Palo Alto, Calif. USA, catalog no. 64018-1, following the protocol described in "Instruction Manual: Superscript® Lambda System for cDNA Synthesis and λ cloning," cat. No. 19643-014, Life Technologies, Gaithersburg, Md., USA which is herein incorporated by reference. Unless otherwise noted, all reagents were also obtained from Life Technologies. The overall procedure can be summarized into the following steps: (1) First strand synthesis; (2) Second strand synthesis; (3) Adaptor addition; (4) Enzymatic digestion; (5) Gel isolation of cDNA; (6) Ligation into vector; and (7) Transformation.

First Strand Synthesis:

Not1 primer-adapter (Life Tech., 2 $\mu$l, 0.5 $\mu$g/$\mu$l) was added to a sterile 1.5 ml microcentrifuge tube to which was added poly A+mRNA (7 $\mu$l, 5 $\mu$g). The reaction tube was heated to 70° C. for 5 minutes or time sufficient to denature the secondary structure of the MRNA. The reaction was then chilled on ice and 5× First strand buffer (Life Tech., 4 $\mu$l), 0.1 M DTT (2 $\mu$l) and 10 mM dNTP Mix (Life Tech., 1 $\mu$l) were added and then heated to 37° C. for 2 minutes to equilibrate the temperature. Superscript II® reverse transcriptase (Life Tech., 5 $\mu$l) was then added, the reaction tube mixed well and incubated at 37° C. for 1 hour, and terminated by placement on ice. The fmal concentration of the reactants was the following: 50 mM Tris-HCl (pH 8.3); 75 mM KCl; 3 mM MgCl$_2$; 10 mM DTT; 500 $\mu$M each dATP, dCTP, dGTP and dTTP; 50 $\mu$g/ml Not 1 primer-adapter; 5 $\mu$g (250 $\mu$g/ml) mRNA; 50,000 U/ml Superscript II® reverse transcriptase.

Second Strand Synthesis:

While on ice, the following reagents were added to the reaction tube from the first strand synthesis, the reaction well mixed and allowed to react at 16° C. for 2 hours, taking care not to allow the temperature to go above 16° C.: distilled water (93 $\mu$l); 5× Second strand buffer (30 $\mu$l); dNTP mix (3 $\mu$l); 10 U/$\mu$l E. Coli DNA ligase (1 $\mu$l); 10 U/$\mu$l E. Coli DNA polymerase I (4 $\mu$l); 2 U/$\mu$l E. Coli RNase H (1 $\mu$l). 10 U T4 DNA Polymerase (2 $\mu$l) was added and the reaction continued to incubate at 16° C. for another 5 minutes. The final concentration of the reaction was the following: 25 mM Tris-HCl (pH 7.5); 100 mM KCl; 5 mM MgCl$_2$; 10 mM (NH$_4$)$_2$SO$_4$; 0.15 mM $\beta$-NAD+; 250 $\mu$M each DATP, dCTP, dGTP, dTTP; 1.2 mM DTT; 65 U/ml DNA ligase; 250 U/ml DNA polymerase I; 13 U/ml Rnase H. The reaction has halted by placement on ice and by addition of 0.5 M EDTA (10 $\mu$l), then extracted through phenol:chloroform:isoamyl alcohol (25:24:1, 150 $\mu$l). The aqueous phase was removed, collected and diluted into 5M NaCl (15 $\mu$l) and absolute ethanol (-20° C., 400 $\mu$l) and centrifuged for 2 minutes at 14,000×g. The supernatant was carefully removed from the resulting DNA pellet, the pellet resuspended in 70% ethanol (0.5 ml) and centrifuged again for 2 minutes at 14,000×g. The supernatant was again removed and the pellet dried in a speedvac.

Adapter Addition

The following reagents were added to the cDNA pellet from the Second strand synthesis above, and the reaction was gently mixed and incubated at 16° C. for 16 hours: distilled water (25 $\mu$l); 5× T4 DNA ligase buffer (10 $\mu$l); Sal 1 adapters (10 $\mu$l); T4 DNA ligase (5 $\mu$l). The final composition of the reaction was the following: 50 mM Tris-HCl (pH 7.6); 10 mM MgCl$_2$; 1 mM ATP; 5% (w/v) PEG 8000; 1 mM DTT; 200 $\mu$g/ml Sal 1 adapters; 100 U/ml T4 DNA ligase. The reaction was extracted through phenol:chloroform:isoamyl alcohol (25:24:1, 50 $\mu$l), the aqueous phase removed, collected and diluted into 5M NaCl (8 $\mu$l) and absolute ethanol (-20° C., 250 $\mu$l). This was then centrifuged for 20 minutes at 14,000×g, the supernatant removed and the pellet was resuspended in 0.5 ml 70% ethanol, and centrifuged again for 2 minutes at 14,000×g. Subsequently, the supernatant was removed and the resulting pellet dried in a speedvac and carried on into the next procedure.

Enzymatic Digestion;

To the cDNA prepared with the Sal 1 adapter from the previous paragraph was added the following reagents and the mixture was incubated at 37° C. for 2 hours: DEPC-treated water (41 $\mu$l); Not 1 restriction buffer (REACT, Life Tech., 5 $\mu$l), Not 1 (4 $\mu$l). The final composition of this reaction was the foUowing: 50 mM Tris-HCl (pH 8.0); 10 mM MgCl$_2$; 100 mM MaCl; 1,200 U/ml Not 1.

Gel Isolation of cDNA:

The cDNA is size fractionated by acrylamide gel electrophoresis on a 5% acrylamide gel, and any fragments which were larger than 1 Kb, as determined by comparison with a molecular weight marker, were excised from the gel. The cDNA was then electroeluted from the gel into 0.1×TBE buffer (200 $\mu$l) and extracted with phenol:chloroform:isoamyl alcohol (25:24:1, 200 $\mu$l). The aqueous phase was removed, collected and centrifuged for 20 minutes at 14,000×g. The supernatant was removed from the DNA pellet which was resuspended in 70% ethanol (0.5 ml) and centrifuged again for 2 minutes at 14,000×g. The supernatant was again discarded, the pellet dried in a speedvac and resuspended in distilled water (15 μl).

Ligation of cDNA into pRK5 Vector:

The following reagents were added together and incubated at 16° C. for 16 hours: 5× T4 ligase buffer (3 μl); pRK5, Xho1, Not1 digested vector, 0.5 μg, 1 μl); cDNA prepared from previous paragraph (5 μl) and distilled water (6 μl). Subsequently, additional distilled water (70 μl) and 10 mg/ml tRNA (0.1 μl) were added and the entire reaction was extracted through phenol:chloroforn:isoamyl alcohol (25:24:1). The aqueous phase was removed, collected and diluted into 5M NaCl (10 μl) and absolute ethanol (−20° C., 250 μl). This was then centrifuged for 20 minutes at 14,000× g, decanted, and the pellet resuspended into 70% ethanol (0.5 ml) and centrifuged again for 2 minutes at 14,000×g. The DNA pellet was then dried in a speedvac and eluted into distilled water (3 μl) for use in the subsequent procedure.

DNA is isolated and transformed into yeast cells that do not contain an invertase gene. Recombinants containing the nonsecreted yeast invertase gene ligated to a mammalian signal sequence are identified based upon their ability to grow on a medium containing only sucrose or only raffinose as the carbon source. The mammalian signal sequences identified are then used to screen a second, full-length cDNA library to isolate the full-length clones encoding the corresponding secreted proteins. Cloning may, for example, be performed by expression cloning or by any other technique known in the art.

The primers used for the identification of FL139 are as follows:

```
OLI114   CCACGTTGGCTTGAAATTGA                                    SEQ ID.NO:13

OLI115   CCTCCAGAATTGATCAAGACAATTCATGATTTGATTCTCTATCTCCAGAG      SEQ.ID NO:14

OLI116   TCGTCTAACATAGCAAATC                                     SEQ.ID NO:15
```

Transformation of Library Ligation into Bacteria:

The ligated cDNA/pRK5 vector DNA prepared previously was chilled on ice to which was added electrocompetent DH10B bacteria (Life Tech., 20 μl). The bacteria vector mixture was then electroporated as per the manufacturers recommendation. Subsequently SOC media (1 ml) was added and the mixture was incubated at 37° C. for 30 minutes. The transformants were then plated onto 20 standard 150 mm LB plates containing ampicillin and incubated for 16 hours (370° C.) to allow the colonies to grow. Positive colonies were then scraped off and the DNA isolated from the bacterial pellet using standard CsCl-gradient protocols. For example, Ausubel et al., 2.3.1.

Identification of FLS139

FLS139 can be identified in the human fetal liver library by any standard method known in the art, including the methods reported by Klein R.D. et al. (1996), *Proc. Natl. Acad Sci.* 93, 7108–7113 and Jacobs (U.S. Pat. No. 5,563,637 issued Jul. 16, 1996). According to Klein et al. and Jacobs, cDNAs encoding novel secreted and membrane-bound mammalian proteins are identified by detecting their secretory leader sequences using the yeast invertase gene as a reporter system. The enzyme invertase catalyzes the breakdown of sucrose to glucose and fructose as well as the breakdown of raffinose to sucrose and melibiose. The secreted form of invertase is required for the utilization of sucrose by yeast (*Saccharomyces cerevisiae*) so that yeast cells that are unable to produce secreted invertase grow poorly on media containing sucrose as the sole carbon and energy source. Both Klein R. D., supra, and Jacobs, supra, take advantage of the known ability of mammalian signal sequences to functionally replace the native signal sequence of yeast invertase. A mammalian cDNA library is ligated to a DNA encoding a nonsecreted yeast invertase, the ligated The nucleotide sequence of FLS139 in shown in FIG. 6 (SEQ. ID. NO: 5), while its amino acid sequence is shown in FIG. 7 (SEQ. ID. NO:6). As illustrated in FIG. 1, FLS139 contains a fibrinogen-like domain exhibiting a high degree of sequence homology with the two known human ligands of the TIE-2 receptor (h-TIE2L1 and h-TIE2L2). Accordingly, FLS139 has been identified as a novel member of the TIE ligand family.

A clone of FLS139 was deposited with the American Type Culture Collection (ATCC), 10801 University Boulevard, Manassas, Va. 20110-2209, on Sep. 18, 1997 under the terms of the Budapest Treaty, and has been assigned the deposit number ATCC 209281.

EXAMPLE 2

Identification of NL2 and NL3

NL2 and NL3 were by screening the GenBank database using the computer program BLAST (Altshul et al., *Methods in Enzymology* 266:460–480 (1996). The NL2 sequence shows homology with known EST sequences T08223, AA122061, and M62290. Similarly, NL3 shows homology with the known EST sequences T57280, and T50719. None of the known EST sequences have been identified as full length sequences, or described as ligands associated with the TIE receptors.

Following their identification, NL2 and NL3 were cloned from a human fetal lung library prepared from mRNA purchased from Clontech, Inc. (Palo Alto, Calif., USA), catalog #6528-1, following the manufacturer's instructions. The library was screened by hybridization with synthetic oligonucleotide probes:

For NL2:

```
NL2,5-1   ATGAGGTGGCCAAGCCTGCCCGAAGAAAGAGGC        SEQ.ID.NO:7

NL2,3-1   CAACTGGCTGGGCCATCTCGGGCAGCCTCTTTCTTCGGG  SEQ.ID.NO:8

NL2,3-4   CCCAGCCAGAACTCGCCGTGGGGA                 SEQ.ID.NO:9

NL3,5-1   TGGTTGGCAAAGGCAAGGTGGCTGACGATCCGG        SEQ.ID.NO:10
```

```
-continued

NL3,3-1  GTGGCCCTTATCTCTCCTGTACAGCTTCCGGATCGTCAGCCAC      SEQ.ID.NO:11

NL3,3-2  TCCATTCCCACCTATGACGCTGACCCA                      SEQ.ID.NO:12
``` based on the ESTs found in the GenBank database. cDNA sequences were sequences in their entireties.

The nucleotide and amino acid sequences of NL2 are shown in FIG. 2 (SEQ. ID. NO: 1) and FIG. 3 (SEQ. ID. NO: 2), respectively. The nucleotide and amino acid sequences of NL3 are shown in FIG. 4 (SEQ. ID. NO: 3) and FIG. 5 (SEQ. ID. NO: 4), respectively.

Collection (ATCC), 10801 University Boulevard, Manassas, Va. 20110-2209, on Sep. 18, 1997 under the terms of the Budapest Treaty, and has been assigned deposit number ATCC 209284.

University Boulevard, Manassas, Va. 20110-2209, on Sep. 18, 1997 under the terms of the Budapest Treaty, and has been assigned deposit number ATCC 209283.

EXAMPLE 3

Northern Blot Analysis

Expression of the FLS139, NL2 and NL3 MRNA in human tissues was examined by Northern blot analysis. Human mRNA blots were hybridized to a $^{32}$P-labeled DNA probe based on the full length cDNAs; the probes were generated by digesting and purifying the cDNA inserts. Human fetal RNA blot MTN (Clontech) and human adult RNA blot MTN-II (Clontech) were incubated with the DNA probes. Blots were incubated with the probes in hybridization buffer (5× SSPE; 2Denhardt's solution; 100 mg/mL denatured sheared salmon sperm DNA; 50% formamide; 2% SDS) for 60 hours at 42° C. The blots were washed several times in 2× SSC; 0.05% SDS for 1 hour at room temperature, followed by a 30 minute wash in 0.1 × SSC; 0.1% SDS at 50° C. The blots were developed after overnight exposure by phosphorimager analysis (Fuji).

Figure 8:
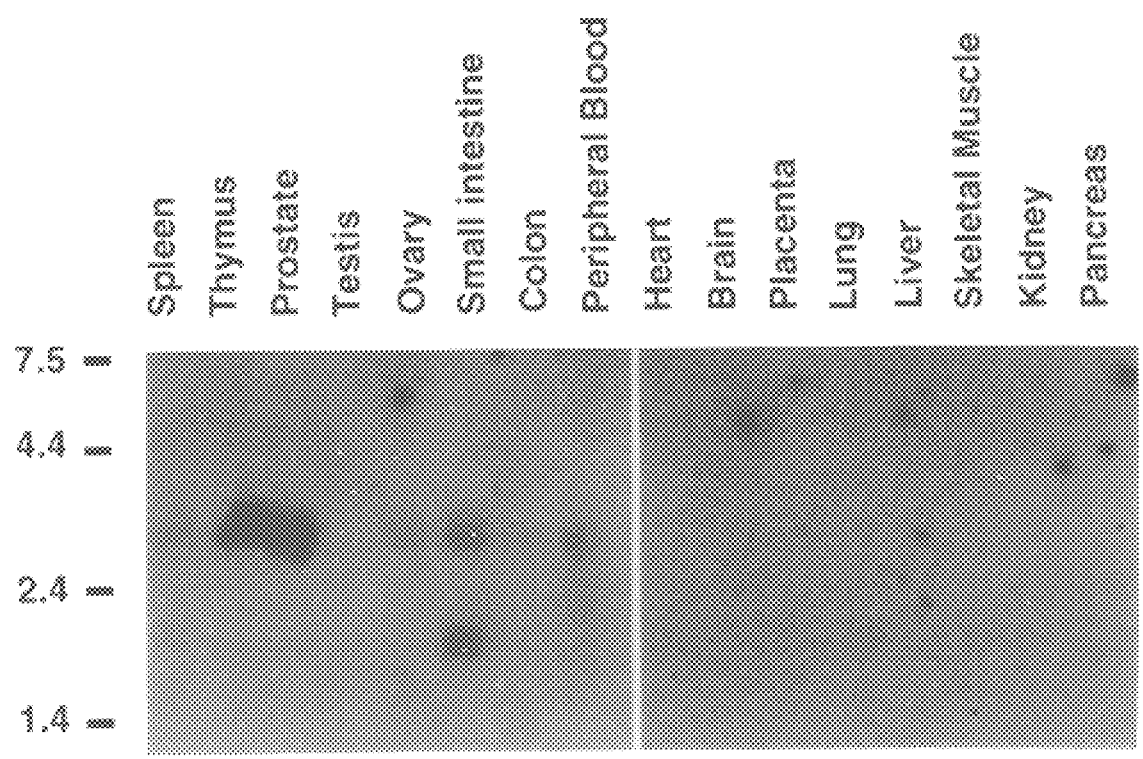
FIGS. 8–9—Northern blots showing the expression of the mRNAs of TIE ligands NL2 and NL3 in various tissues.
Figure 9:
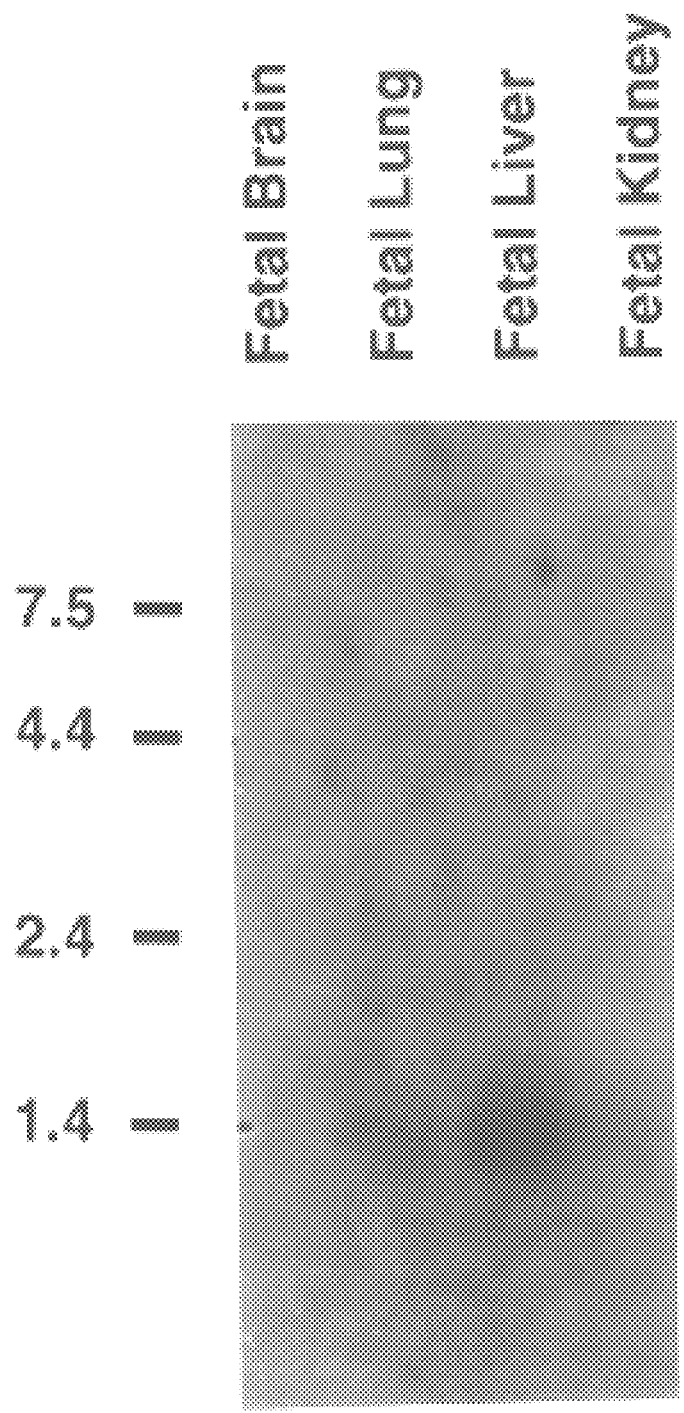

As shown in FIGS. 8 and 9, NL2 and NL3 MRNA transcripts were detected.

EXAMPLE 4

Expression of FLS139, NL-2 and NL-3 in *E. coli*

This example illustrates the preparation of an unglycosylated form of the TIE ligands homologues of the present invention in *E. coli*. The DNA sequence encoding a NL-2, NL-3 or FLS139 ligand (SEQ. ID. NOs: 1, 3, and 5, respectively) is initially amplified using selected PCR primers. The primers should contain restriction enzyme sites which correspond to the restriction enzyme sites on the selected expression vector. A variety of expression vectors may be employed. The vector will preferably encode an antibiotic resistance gene, an origin of replication, e promoter, and a ribozyme binding site. An example of a suitable vector is pBR322 (derived from *E. coli*; see Bolivar et al., *Gene* 2:95 (1977)) which contains genes for ampicillin and tetracycline resistance. The vector is digested with restriction enzyme and dephosphorylated. The PCR amplified sequences are then ligated into the vector.

The ligation mixture is then used to transform a selected *E. coli* strain, such as . . . , using the methods described in Sambrook et al., supra. Transformants are identified by their ability to grow on LB plates and antibiotic resistant colonies are then selected. Plasmid DNA can be isolated and confirmed by restriction analysis.

Selected clones can be grown overnight in liquid culture medium such as 1B broth supplemented with antibiotics. The overnight culture may subsequently be used to inoculate a later scale culture. The cells are then grown to a desired optical density. An inducer, such as IPTG may be added.

After culturing the cells for several more hours, the cells can be harvested by centrifugation. The cell pellet obtained by the centrifugation can be solubilized using various agents known in the art, and the solubilized protein can then be purified using a metal chelating column under conditions that allow tight binding of the protein.

EXAMPLE 5

Expression of FLS139, NL2 and NL3 in Mammalian Cells

This example illustrates preparation of a glycosylated form of the FLS139, NL2 and NL3 ligands by recombinant expression in mammalian cells.

The vector, pRK5 (see EP 307,247, published Mar. 15, 1989), is employed as the expression vector. Optionally, the FLS139, NL2 and NL3 DNA is ligated into pRK5 with selected restriction enzymes to allow insertion of the FLS139, NL2 and NL3 DNA using ligation methods such as described in Sambrook et al., supra. The resulting vector is called pRK5-FLS139, -NL2 and NL3, respectively.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-FLS139, -NL2 and NL-3 DNA is mixed with about 1 μg DNA encoding the VA RNA gene [Thimmappaya et al., *Cell*, 31:543 (1982)] and dissolved in 500 μl of 1 mM Tris-HCl, 0.1 MM EDTA, 0.227 M CaCl$_2$. To this mixture is added, dropwise, 500 μl of 50 mM HEPES (pH 7.35), 280 mM NaCl, 1.5 mM NaPO$_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of FLS139, NL2 and NL3 polypeptide. The cultures containing transfected cells may undergo further incubation (in serum free medium) and the medium is tested in selected bioassays.

In an alternative technique, FLS139, NL2 and NL3 may be introduced into 293 cells transiently using the dextran sulfate method described by Somparyrac et al., *Proc. Natl. Acad. Sci.*, 12:7575 (1981). 293 cells are grown to maximal density in a spinner flask and 700 µg pRK5-FLS139, -NL2 and -NL3 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed FLS139, NL2 and NL3 can then be concentrated and purified by any selected method, such as dialysis and/or column chromatography.

In another embodiment, FLS139, NL2 and NL3 can be expressed in CHO cells. The pRK5-FLS139, -NL2 and -NL3 can be transfected into CHO cells using known reagents such as $CaPO_4$ or DEAE-dextran. As described above, the cell cultures can be incubated, and the medium replaced with culture medium (alone) or medium containing a radiolabel such as $^{35}S$-methionine. After determining the presence of FLS139, NL2 and NL3 polypeptide, the culture medium may be replaced with serum free medium. Preferably, the cultures are incubated for about 6 days, and then the conditioned medium is harvested. The medium containing the expressed FLS139, NL2 and NL3 can then be concentrated and purified by any selected method.

Epitope-tagged FLS139, NL2 and NL3 may also be expressed in host CHO cells. FLS139, NL2 and NL3 may be subcloned out of the pRK5 vector. The subclone insert can undergo PCR to fuse in frame with a selected epitope tag such as a poly-his tag into a Baculovirus expression vector. The poly-his tagged FLS139, NL2 and NL3 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged FLS139, NL2 and NL3 can then be concentrated and purified by any selected method, such as by $Ni^{2+}$-chelate affinity chromatography.

EXAMPLE 6

Expression of FLS139, NL2 and NL3 in Yeast

First, yeast expression vectors are constructed for intracellular production or secretion of FLS139, NL2 and NL3 from the ADH2/GAPDH promoter. DNA encoding FLS139, NL2 and NL3, a selected signal peptide and the promoter is inserted into suitable restriction enzyme sites in the selected plasmid to direct intracellular expression of FLS139, NL2 and NL3. For secretion, DNA encoding FLS139, NL2 and NL3 can be cloned into the selected plasmid, together with DNA encoding the ADH2/GAPDH promoter, the yeast alpha-factor secretory signal/leader sequence, and linker sequences (if needed) for expression of FLS139, NL2 and NL3.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant FLS139, NL2 and NL3 can subsequently be isolated and purified by removing the yeast cells from the fermentation medium by centrifugation and then concentrating the medium using selected cartridge filters. The concentrate containing FLS139, NL2 and NL3 may further be purified using selected column chromatography resins.

EXAMPLE 7

Expression of FLS139, NL2 and NL3 in Baculovirus

The following method describes recombinant expression of FLS139, NL2 and NL3 in Baculovirus.

The FLS139, NL2 and NL3 is fused upstream of an epitope tag contained with a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the FLS139, NL2 and NL3 or the desired portion of the FLS139, NL2 and NL3 (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged FLS139, NL2 and NL3 can then be purified, for example, by $Ni^{2+}$-chelate affinity chromatography as follows. Extracts are prepared from recombinant virus-infected Sf9 cells as described by Rupert et al., *Nature*, 362:175–179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged FLS139, NL2 and NL3 are pooled and dialyzed against loading buffer.

Alternatively, purification of the IgG tagged (or Fc tagged) FLS139, NL2 and NL3 can be performed using known chromatography techniques, including for instance, Protein A or protein G column chromatography.

EXAMPLE 8

Preparation of Antibodies that Bind FLS139, NL2, or NL3

This example illustrates preparation of monoclonal antibodies which can specifically bind FLS139, NL2, or NL3.

Techniques for producing the monoclonal antibodies are known in the art and are described, for example, in Goding, supra. Immunogens that may be employed include purified ligands of the present invention, fusion proteins containing such ligands, and cells expressing recombinant ligands on the cell surface. Selection of the immunogen can be made by the skilled artisan without undue experimentation.

Mice, such as Balb/c, are immunized with the immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind food pads. The immunized mice are then boosted 10 to 12 days later with additional immunogen emulsified in the selected adjuvant. Thereafter, for several weeks, the mice might also be boosted with additional immunization injections. Serum samples may be periodically obtained from the mice by retro-orbital bleeding for testing ELISA assays to detect the antibodies.

After a suitable antibody titer has been detected, the animals "positive" for antibodies can be injected with a final intravenous injection of the given ligand. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against the antigen. Determination of "positive" hybridoma cells secreting the desired monoclonal antibodies against the TIE ligands herein is well within the skill in the art.

The positive hybridoma cells can be injected intraperitoneal into syngeneic Balb/c mice to produce ascites containing the anti-TIE-ligand monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Deposit of Material

As noted before, the following materials have been deposited with the American Type Culture Collection, 10801 University Boulevard, Manassas, Va. 20110-2209, USA (ATCC):

| Material | ATCC Dep. No. | Deposit Date |
| --- | --- | --- |
| NL2-DNA 22780-1078 | 209284 | September 17, 1997 |
| NL3-DNA 33457-1078 | 209283 | September 18, 1997 |
| FLS 139-DNA 16451-1978 | 209281 | September 18, 1997 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of the deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and Commissioner's rules pursuant thereto (including 37 C.F.R. § 1.14 with particular reference to 886 OG 683).

The assignee of the present application has agreed that if a culture of the materials on deposit should die ot be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The present specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of the invention. The deposit of material herein does not constitute an admission that the written description is inadequate to enable the practice of any aspect of the invention, including the best more thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

We claim:

1. An isolated nucleic acid molecule which comprises the coding region of SEQ ID NO:5.

2. A vector which comprises the nucleic acid molecule of claim 1.

3. A recombinant host cell transformed with the nucleic acid molecule of claim 1.

4. The recombinant host cell of claim 3 which is a prokaryotic cell.

5. The recombinant host cell of claim 3 which is a eukaryotic cell.

6. An isolated nucleic acid molecule comprising a nucleic acid encoding an FLS139 polypeptide having the sequence of SEQ ID NO: 6.

7. A vector which comprises the nucleic acid molecule of claim 6.

8. A recombinant host cell transformed with the nucleic acid molecule of claim 6.

9. The recombinant host cell of claim 8 which is a prokaryotic cell.

10. The recombinant host cell of claim 8 which is a eukaryotic cell.

11. An isolated nucleic acid molecule comprising a nucleic acid encoding a polypeptide having the sequence of amino acids 238 to 460 of SEQ ID NO: 6.

12. A vector which comprises the nucleic acid molecule of claim 11.

13. A recombinant host cell transformed with the nucleic acid molecule of claim 11.

14. The recombinant host cell of claim 13 which is a prokaryotic cell.

15. The recombinant host cell of claim 13 which is a eukaryotic cell.

* * * * *